(12) United States Patent
Thubrikar et al.

(10) Patent No.: US 10,575,945 B2
(45) Date of Patent: Mar. 3, 2020

(54) VALVE COMPONENT, FRAME COMPONENT AND PROSTHETIC VALVE DEVICE INCLUDING THE SAME FOR IMPLANTATION IN A BODY LUMEN

(71) Applicant: Thubrikar Aortic Valve, Inc., Norristown, PA (US)

(72) Inventors: Mano J. Thubrikar, North Wales, PA (US); Yogesh Darekar, Santa Rosa, CA (US)

(73) Assignee: THUBRIKAR AORTIC VALVE, INC., Rapid City, SD (US)

( * ) Notice: Subject to any disclaimer, the term of this patent is extended or adjusted under 35 U.S.C. 154(b) by 213 days.

(21) Appl. No.: 15/877,736

(22) Filed: Jan. 23, 2018

(65) Prior Publication Data

US 2018/0243088 A1    Aug. 30, 2018

Related U.S. Application Data

(63) Continuation of application No. 15/413,617, filed on Jan. 24, 2017, now Pat. No. 9,872,764, which is a continuation of application No. 14/539,173, filed on Nov. 12, 2014, now Pat. No. 9,549,814, which is a continuation of application No. 13/637,282, filed as application No. PCT/US2011/030217 on Mar. 28, 2011, now Pat. No. 8,992,599.

(Continued)

(51) Int. Cl.
*A61F 2/24* (2006.01)
*B32B 1/08* (2006.01)
*B32B 7/08* (2019.01)
*B32B 7/12* (2006.01)
*B32B 25/00* (2006.01)
*B32B 37/16* (2006.01)

(52) U.S. Cl.
CPC .......... *A61F 2/2415* (2013.01); *A61F 2/2403* (2013.01); *A61F 2/2409* (2013.01); *A61F 2/2418* (2013.01); *B32B 1/08* (2013.01); *B32B 7/08* (2013.01); *B32B 7/12* (2013.01); *B32B 25/00* (2013.01); *B32B 37/16* (2013.01); *A61F 2210/0076* (2013.01); *A61F 2220/005* (2013.01); *A61F 2220/0025* (2013.01); *A61F 2220/0066* (2013.01); *A61F 2220/0075* (2013.01); *A61F 2230/0054* (2013.01); *B32B 2307/70* (2013.01); *B32B 2535/00* (2013.01)

(58) Field of Classification Search
CPC ........ A61F 2/24; A61F 2/2415; A61F 2/2403; A61F 2/2409; A61F 2/2418; A61F 2/2427; A61F 2/2445; A61F 2/2436; B32B 1/08; B32B 7/08; B32B 7/12; B32B 25/00; B32B 37/16
See application file for complete search history.

(56) References Cited

U.S. PATENT DOCUMENTS

| 4,118,806 A | 10/1978 | Porier et al. |
| 4,350,492 A | 9/1982 | Wright et al. |

(Continued)

*Primary Examiner* — Alvin J Stewart
(74) *Attorney, Agent, or Firm* — The Belles Group, P.C.

(57) ABSTRACT

Described herein is a prosthetic valve device having an optimized valve component for durability and functionality of the collapsible leaflets. Specially designed commissures contribute to the optimization along with identified parameters. In other embodiments, the invention is a frame formed from a unique cutting pattern.

11 Claims, 14 Drawing Sheets

Related U.S. Application Data

(60) Provisional application No. 61/318,218, filed on Mar. 26, 2010.

(56) References Cited

U.S. PATENT DOCUMENTS

| | | |
|---|---|---|
| 4,501,030 A | 2/1985 | Lane |
| 5,840,081 A | 11/1998 | Andersen et al. |
| 5,925,063 A | 7/1999 | Khosravi |
| 5,954,766 A | 9/1999 | Zadno-Azizi et al. |
| 5,957,949 A | 9/1999 | Leonhardt et al. |
| 6,074,419 A | 6/2000 | Healy et al. |
| 6,168,614 B1 | 1/2001 | Andersen et al. |
| 6,221,091 B1 | 4/2001 | Khosravi |
| 6,264,691 B1 | 7/2001 | Gabbay |
| 6,287,334 B1 | 9/2001 | Moll et al. |
| 6,299,637 B1 | 10/2001 | Shaolian et al. |
| 6,425,916 B1 | 7/2002 | Garrison et al. |
| 6,458,153 B1 * | 10/2002 | Bailey .................. A61F 2/2418 623/1.24 |
| 6,478,819 B2 | 11/2002 | Moe |
| 6,494,909 B2 | 12/2002 | Greenhalgh |
| 6,517,576 B2 | 2/2003 | Gabbay |
| 6,562,069 B2 | 5/2003 | Cai et al. |
| 6,582,462 B1 | 6/2003 | Andersen et al. |
| 6,652,578 B2 | 11/2003 | Bailey et al. |
| 6,669,724 B2 | 12/2003 | Park et al. |
| 6,733,525 B2 | 5/2004 | Yang et al. |
| 6,830,584 B1 | 12/2004 | Seguin |
| 6,840,957 B2 | 1/2005 | DiMatteo et al. |
| 6,908,481 B2 * | 6/2005 | Cribier .................. A61F 2/2412 623/2.11 |
| 6,958,076 B2 | 10/2005 | Acosta et al. |
| 6,974,464 B2 | 12/2005 | Quijano et al. |
| 7,125,418 B2 | 10/2006 | Duran et al. |
| 7,153,324 B2 | 12/2006 | Case et al. |
| 7,160,320 B2 | 1/2007 | Duran |
| 7,201,772 B2 | 4/2007 | Schwammenthal et al. |
| 7,252,682 B2 | 8/2007 | Seguin |
| 7,261,732 B2 | 8/2007 | Justino |
| 7,267,686 B2 | 9/2007 | DiMatteo et al. |
| 7,291,167 B2 | 11/2007 | DiCaprio |
| 7,338,520 B2 | 3/2008 | Bailey et al. |
| 7,351,256 B2 | 4/2008 | Hojeibane et al. |
| 7,361,189 B2 | 4/2008 | Case et al. |
| 7,377,938 B2 | 5/2008 | Sarac et al. |
| 7,458,987 B2 | 12/2008 | Case et al. |
| 7,510,575 B2 | 3/2009 | Spenser et al. |
| 7,547,322 B2 | 6/2009 | Sarac et al. |
| 7,618,446 B2 | 11/2009 | Andersen et al. |
| 7,846,199 B2 | 12/2010 | Paul, Jr. et al. |
| 8,038,710 B2 | 10/2011 | Fearnot et al. |
| 8,092,518 B2 | 1/2012 | Schreck |
| 8,157,860 B2 | 4/2012 | McNamara et al. |
| 8,172,896 B2 | 5/2012 | McNamara et al. |
| 8,226,710 B2 | 7/2012 | Nguyen et al. |
| 8,246,675 B2 | 8/2012 | Zegdi |
| 8,246,676 B2 | 8/2012 | Acosta et al. |
| 8,252,042 B2 | 8/2012 | McNamara et al. |
| 8,303,649 B2 | 11/2012 | Agnew et al. |
| 8,398,704 B2 * | 3/2013 | Straubinger .......... A61F 2/2418 623/1.15 |
| 8,500,821 B2 | 8/2013 | Sobrino-Serrano et al. |
| 8,623,078 B2 | 1/2014 | Salahieh et al. |
| 8,992,599 B2 * | 3/2015 | Thubrikar ............. A61F 2/2415 623/1.26 |
| 9,034,032 B2 * | 5/2015 | McLean ................ A61F 2/2427 623/2.12 |
| 9,549,814 B2 * | 1/2017 | Thubrikar ............. A61F 2/2415 |
| 9,872,764 B2 * | 1/2018 | Thubrikar ............. A61F 2/2415 |
| 10,058,424 B2 * | 8/2018 | Cooper ................. A61F 2/2418 |
| 10,226,330 B2 * | 3/2019 | Spence ................. A61F 2/2418 |
| 10,226,339 B2 * | 3/2019 | Spence ................. A61F 2/2418 |
| 10,232,564 B2 * | 3/2019 | Pelled ............... B29C 66/53245 |
| 2002/0077698 A1 | 6/2002 | Peredo |
| 2003/0109923 A1 | 6/2003 | Chinn et al. |
| 2003/0109924 A1 | 6/2003 | Cribier |
| 2004/0098112 A1 | 5/2004 | DiMatteo et al. |
| 2004/0236411 A1 | 11/2004 | Sarac et al. |
| 2004/0260390 A1 | 12/2004 | Sarac et al. |
| 2005/0075718 A1 | 4/2005 | Nguyen et al. |
| 2005/0096738 A1 | 5/2005 | Cali et al. |
| 2005/0137681 A1 | 6/2005 | Shoemaker et al. |
| 2005/0137682 A1 | 6/2005 | Justino |
| 2005/0187618 A1 | 8/2005 | Gabbay |
| 2005/0222674 A1 | 10/2005 | Paine |
| 2006/0122686 A1 | 6/2006 | Gilad et al. |
| 2006/0122693 A1 | 6/2006 | Biadillah et al. |
| 2006/0167543 A1 | 7/2006 | Bailey et al. |
| 2006/0190074 A1 | 8/2006 | Hill et al. |
| 2006/0229719 A1 | 10/2006 | Marquez et al. |
| 2006/0259135 A1 | 11/2006 | Navia et al. |
| 2006/0259136 A1 | 11/2006 | Nguyen et al. |
| 2006/0276874 A1 | 12/2006 | Wilson et al. |
| 2006/0287719 A1 | 12/2006 | Rowe et al. |
| 2007/0208550 A1 | 9/2007 | Cao et al. |
| 2008/0082166 A1 | 4/2008 | Styrc et al. |
| 2008/0154356 A1 | 6/2008 | Obermiller et al. |
| 2008/0275540 A1 | 11/2008 | Wen |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0240320 A1 | 9/2009 | Tuval et al. |
| 2009/0270972 A1 | 10/2009 | Lane |
| 2009/0287298 A1 | 11/2009 | Jenson et al. |
| 2009/0292350 A1 | 11/2009 | Eberhardt et al. |
| 2010/0004727 A1 | 1/2010 | Andersen et al. |
| 2010/0011564 A1 | 1/2010 | Millwee et al. |
| 2010/0030324 A1 | 2/2010 | Seguin et al. |
| 2010/0082094 A1 * | 4/2010 | Quadri .................. A61F 2/2412 623/1.26 |
| 2010/0204781 A1 | 8/2010 | Alkhatib |
| 2010/0249894 A1 | 9/2010 | Oba et al. |
| 2011/0040375 A1 | 2/2011 | Letac et al. |
| 2013/0204359 A1 * | 8/2013 | Thubrikar ............. A61F 2/2415 623/2.17 |
| 2013/0325114 A1 * | 12/2013 | McLean ................ A61F 2/2427 623/2.12 |
| 2013/0345786 A1 | 12/2013 | Behan |
| 2015/0073543 A1 * | 3/2015 | Thubrikar ............. A61F 2/2415 623/2.17 |
| 2016/0184095 A1 * | 6/2016 | Spence ................. A61F 2/2418 623/2.11 |
| 2017/0128202 A1 * | 5/2017 | Thubrikar ............. A61F 2/2415 |
| 2018/0206982 A1 * | 7/2018 | Haivatov ............. A61F 2/2409 |
| 2018/0243088 A1 * | 8/2018 | Thubrikar ............. A61F 2/2415 |

* cited by examiner

VALVE COMPONENT, FRAME COMPONENT AND PROSTHETIC VALVE DEVICE INCLUDING THE SAME FOR IMPLANTATION IN A BODY LUMEN

CROSS-REFERENCE TO RELATED PATENT APPLICATIONS

The present application is a continuation of U.S. patent application Ser. No. 15/413,617, filed Jan. 24, 2017, which is a continuation of U.S. patent application Ser. No. 14/539,173, filed Nov. 12, 2014, now U.S. Pat. No. 9,549,814; which is a continuation of U.S. patent application Ser. No. 13/637,282, filed Jan. 23, 2013, now U.S. Pat. No. 8,992,599; which is a U.S. National Application under 35 U.S.C. § 371 of PCT Application No. PCT/US2011/030217, filed Mar. 28, 2011, which in turn claims the benefit of U.S. Provisional Patent Application Ser. No. 61/318,218, filed Mar. 26, 2010, the entireties of which are hereby incorporated herein by reference.

FIELD OF THE DISCLOSURE

The present invention relates generally to prosthetic valve devices for implantation into a body lumen, and specifically to prosthetic valve devices, and components thereof, for implantation into a body lumen via transluminal delivery. While not so limited, the present invention is particularly suited for use in replacing a native heart valve or a failing prosthetic heart valve previously implanted within a patient.

BACKGROUND

Heart valve disease continues to be a significant cause of morbidity and mortality. Heart valve replacement has become a routine surgical procedure for patients suffering from valve regurgitation or stenotic calcification of the leaflets. Until recently, the vast majority of heart valve replacements entailed full sternotomy and placing the patient on cardiopulmonary bypass. Traditional open surgery inflicts significant patient trauma and discomfort, requires extensive recuperation times and may result in life-threatening complications. To address these concerns, within the last fifteen years efforts have been made to perform cardiac valve replacements using minimally-invasive techniques, such as a percutaneous entry with a transluminal delivery. These surgical techniques, generally referred to as percutaneous heart valve replacement therapies (PHVT), use a catheter to deliver a prosthetic valve device to an implantation site using a patients' lumen of the vascular system.

In general, two types of prosthetic heart valve devices are used in the industry to replace defective native heart valves (or a previously implanted prosthetic heart valve that are failing): mechanical prosthetic valve devices and biological prosthetic valve devices. Biological prosthetic valve devices use a natural tissue, typically of porcine or human origin, to form the collapsible leaflets of the biological prosthetic valve device.

While great efforts have been put into developing prosthetic valve devices for cardiac and other body lumens, existing prosthetic valve devices suffer from a number of drawbacks, including premature failure due to wear, complexity of manufacture, and less than optimal performance. Such deficiencies are present both in the valve component and the frame of existing prosthetic valve devices. For example, deficiencies in existing valve components include without limitation: (1) the working leaflets and fluid passageway of the valve component being subjected to anchoring penetrations that can cause premature wear; (2) less than optimal leaflet design that can result in inferior sealing of the fluid passageway; (3) less than optimal leaflet design that can result in undesirable overlap and/or crimping of the collapsible leaflets during a closure state; and (4) complexity of the leaflet. Deficiencies in the frames, which can act as stent components when installed, include without limitation: (1) complexity of manufacture; (2) lack of adequate structural support for commissures; and (3) lack of suitable geometry for properly anchoring a valve component.

Thus, a need exists for an improved prosthetic valve device, an improved valve component, and/or an improved frame, including methods of forming the same.

SUMMARY

In certain aspects, the present invention is directed to a prosthetic valve device that is suitable for implantation in a body lumen, and components thereof, such as the valve component and the frame. In other aspects, the invention is directed to methods of forming a prosthetic valve device, the valve component and/or the frame.

In some embodiments, the invention provides a prosthetic valve device for implantation into a body lumen comprising: a frame comprising a tubular body; and a valve component disposed within the tubular body of the frame, the valve component comprising: an annular sleeve forming a fluid passageway along an axis from a fluid inlet to a fluid outlet; and a plurality of commissures forming a plurality of collapsible leaflets at the fluid outlet for opening and sealing the fluid passageway, each of the commissures anchored to the tubular body of the frame and formed by a cinched portion of the annular sleeve located between opposing legs of a commissure strip.

In other embodiments, the invention provides a valve component to be anchored within a frame for implantation into a body lumen, the valve component comprising: an annular sleeve forming a fluid passageway along an axis from an inlet edge to an outlet edge; and a plurality of commissure strips arranged in a spaced-apart arrangement about a circumference of the outlet edge, each of the commissure strips affixed to and cinching a portion of the annular sleeve between opposing legs of the commissure strip.

In further embodiments, the invention provides a method of forming a prosthetic valve device for implantation into a body lumen comprising: a) forming a valve component by: a1) forming an annular sleeve having a fluid passageway along an axis from an inlet edge to an outlet edge; and a2) affixing a plurality of commissure strips in a spaced-apart arrangement about a circumference of the outlet edge, each of the commissure strips cinching a portion of the annular sleeve between opposing legs of the commissure strip to form a commissure; and b) providing a frame having a tubular body; c) positioning the valve component within the tubular body of the frame; and d) anchoring the commissures to the tubular body of the frame to form a plurality of collapsible leaflets at the outlet edge for opening and sealing the fluid passageway.

Still further embodiments provide a method of forming a valve component for a prosthetic valve device comprising: forming an annular sleeve having a fluid passageway along an axis from an inlet edge to an outlet edge; and affixing a plurality of commissure strips in a spaced-apart arrangement about a circumference of the outlet edge, each of the commissure strips cinching a portion of the annular sleeve between opposing legs of the commissure strip to form a commissure.

In yet other embodiments, the invention provides a prosthetic valve device for implantation into a body lumen comprising: a frame comprising a tubular body; and a valve component disposed within and anchored to the tubular body of the frame, the valve component comprising: an annular sleeve having an annular inner wall that forms a fluid passageway along an axis from an inlet edge to an outlet edge, the annular sleeve folded over at the inlet edge to form an annular cuff that is concentric to and surrounds the annular inner wall and extends from the inlet edge toward the outlet edge; and an annular belt positioned between the annular inner wall and the annular cuff and having a bottom edge adjacent to a bight portion of the annular sleeve that forms the inlet edge.

Some embodiments provide a valve component to be anchored within a frame for implantation into a body lumen, the valve component comprising: an annular sleeve having an annular inner wall that forms a fluid passageway along an axis from an inlet edge to an outlet edge, the annular sleeve folded over at the inlet edge to form an annular cuff that is concentric to and surrounds the annular inner wall and extends from the inlet edge toward the outlet edge; and an annular belt positioned between the annular inner wall and the annular cuff and having a bottom edge adjacent to a bight portion of the annular sleeve that forms the inlet edge.

In still further embodiments, the invention provides a method of forming a prosthetic valve device for implantation into a body lumen comprising: a) forming an annular sleeve; b) affixing an annular belt to the annular sleeve, the annular belt having a bottom edge; c) providing a frame having a tubular body; d) anchoring the annular sleeve and the annular belt within the tubular body of the frame; and e) folding the annular sleeve inward upon itself along the bottom edge of the annular belt so as to form an annular inner wall and an annular cuff that is concentric to and surrounds the annular inner wall, the annular inner wall forming a fluid passageway along an axis from an inlet edge to an outlet edge, the bottom edge of the annular belt adjacent to a bight portion of the annular sleeve that forms the inlet edge.

Other embodiments provide a method of forming a valve component for a prosthetic valve device for implantation into a body lumen comprising: a) forming an annular sleeve; b) affixing an annular belt to the annular sleeve, the annular belt having a bottom edge; c) folding the annular sleeve along the bottom edge of the annular belt so as to form an annular inner wall and an annular cuff that is concentric to and surrounds the annular inner wall, the annular inner wall forming a fluid passageway along an axis from an inlet edge to an outlet edge, wherein the bottom edge of the annular belt is adjacent to a bight portion of the annular sleeve that forms the inlet edge.

In some embodiments, the invention provides a prosthetic valve device for implantation into a body lumen comprising: a frame comprising a tubular body; and a valve component disposed within and anchored to the tubular body of the frame, the valve component comprising: an annular sleeve; an annular inner wall that forms a fluid passageway along an axis from an inlet edge to an outlet edge; a plurality of commissures arranged in a spaced-apart arrangement about a circumference of the outlet edge of the annular inner wall, the commissures forming a plurality of collapsible leaflets for opening and sealing the fluid passageway, the commissures anchored to the tubular body; and wherein with the exception of the commissures, the annular inner wall is free of anchoring penetrations.

Still further embodiments provide a prosthetic valve device for implantation into a body lumen comprising: a frame comprising a tubular body; a valve component disposed within and anchored to the tubular body of the frame, the valve component comprising: an annular sleeve formed from a single sheet of material, the annular sleeve comprising an annular inner wall that forms a fluid passageway along an axis from an inlet edge to an outlet edge, the annular sleeve folded over at the inlet edge to form an annular cuff that is concentric to and surrounds the annular inner wall and extends from the inlet edge toward the outlet edge; and a plurality of commissures arranged in a spaced-apart manner about a circumference of the outlet edge of the annular inner wall, the commissures forming a plurality of collapsible leaflets for opening and sealing the fluid passageway, the commissures anchored to the tubular body.

In yet other embodiments, the invention provides a prosthetic valve device for implantation into a body lumen comprising: a frame comprising a tubular body; and a valve component disposed within and anchored to the tubular body of the frame, the valve component comprising: an annular sleeve comprising an annular inner wall that forms a fluid passageway along an axis from a fluid inlet to a fluid outlet; a plurality of commissures arranged in a spaced-apart manner about a circumference of the fluid outlet and anchored to the tubular body, the commissures forming a plurality of collapsible leaflets for opening and sealing the fluid passageway, wherein the fluid outlet has a first diameter and the fluid inlet has a second diameter that is greater than the first diameter; and wherein the fluid inlet forms a lower plane of a reference truncated cone and the fluid outlet forms an upper plane of the reference truncated cone, the reference truncated cone having a height and being a portion of a 9° to 11° cone, wherein a ratio of the second diameter to the height is in a range of 1.3:1 to 1.5:1.

Yet other embodiments provide a blank for forming a valve component of a prosthetic valve device for implantation into a body lumen, the blank comprising: a single sheet of pliable material comprising a leaflet section comprising an arcuate top edge, an arcuate bottom edge, and linear left and right side edges extending between the arcuate top and bottom edges; the arcuate top and bottom edge extending substantially parallel to one another and the left and right side edges extending at an angle between 31° to 33° with respect to one another.

In still other embodiments, the invention provides a method of forming a tubular body of a frame for a prosthetic valve device comprising: a) cutting a pattern into a tube having a first inner diameter and an axis, the pattern comprising a plurality of post pattern sections arranged on the tube in a circumferentially spaced-apart manner and a plurality of lattice pattern sections extending between the post pattern sections; and b) diametrically expanding the tube until the tube has a second inner diameter that is greater than the first inner diameter, wherein the expanded tube comprises a plurality of axial posts arranged on the expanded tube in a circumferentially spaced-apart manner and a plurality of lattices having open cells extending between the axial posts.

In yet other embodiments, the invention provides a frame for a prosthetic valve device comprising a tubular body comprising an axis, a plurality of circumferentially spaced-apart axial posts and a lattice structure comprising open cells extending between each of the axial posts, and wherein the lattice structures and the axial posts are integrally formed as a unitary structure free of seams.

In further embodiment, the invention provides a prosthetic valve device for implantation into a body lumen comprising: a frame comprising a tubular body; a valve component comprising an annular sleeve having an annular inner wall that forms a fluid passageway along an axis from an inlet edge to an outlet edge, the annular sleeve folded over at the inlet edge to form an annular cuff that is concentric to and surrounds the annular inner wall and extends from the inlet edge toward the outlet edge; and wherein the valve component is disposed within and anchored to the tubular body of the frame, the annular inner wall and the annular cuff positioned within the tubular body of the frame.

While the aforementioned inventions are particularly suited for use as (or in) a prosthetic heart valve, further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

Figure 1:
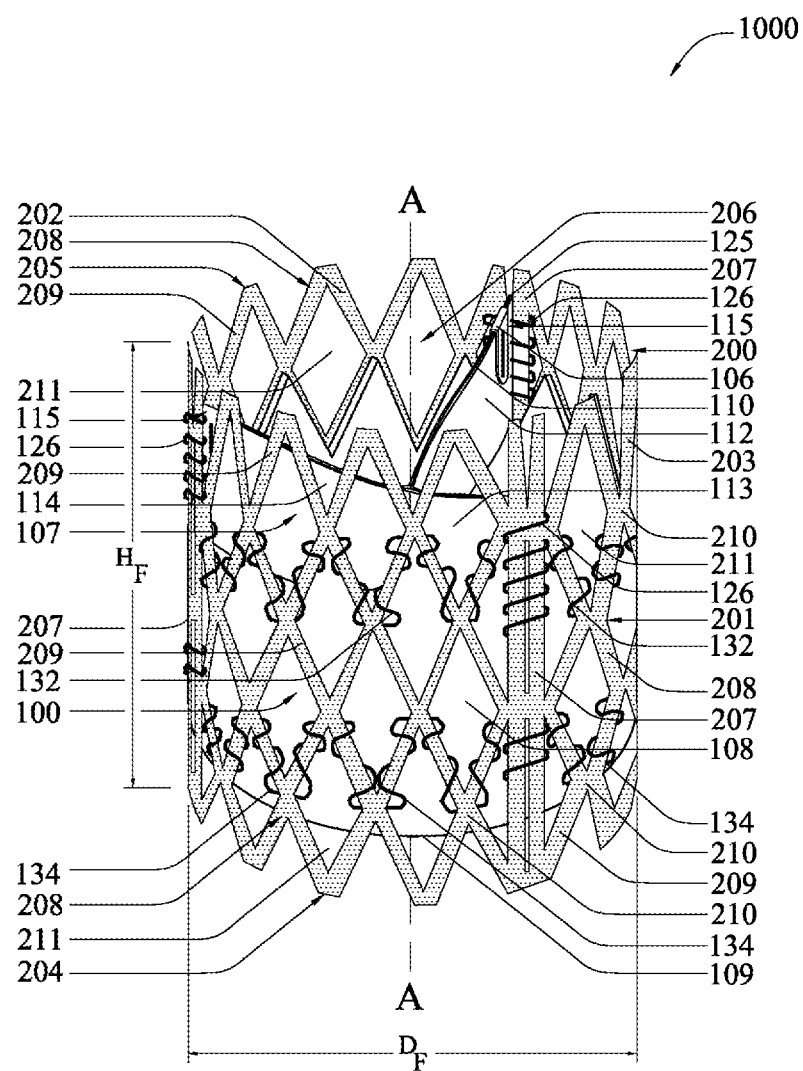
FIG. 1 is a perspective view of a prosthetic valve device according to some embodiments of the present invention.

Referring first to FIG. 1, a prosthetic valve device 1000 is illustrated according to some embodiments of the present invention. The prosthetic valve device 1000 can be used to replace, for example, a failed (e.g., degenerated) aortic valve, mitral valve, or pulmonary cardiac valve (e.g., in a geriatric patient) in accordance with some embodiments of the present invention. Embodiments of the invention, however, are not so limited and the prosthetic valve device 1000 can be used in other body lumens and/or in conjunction with other organs as desired. The prosthetic valve device 1000 can be delivered to the implantation site using any suitable delivery approach, including "open-heart" delivery. However, the prosthetic valve device 1000 is particularly suited for transluminal delivery, either in separate components or as a fully assembled structure.

The prosthetic valve device 1000 generally comprises a valve component 100 and a frame 200. The valve component 100 is disposed within and anchored to a frame 200. The frame 200, in the exemplified embodiment, is a stent component. In those embodiments of the present invention wherein the prosthetic valve device 1000 is designed for transluminal delivery, both the frame 200 and the valve component 100 are capable of at least two configurations: a first, collapsed configuration (e.g., during delivery) and a second, expanded configuration (e.g., after implantation). In FIG. 1, both the valve component 100 and the frame 200 are in an expanded configuration. In the collapsed configuration, the valve component 100 may remain disposed within the frame 200 so that the prosthetic valve device 1000 remains fully assembled prior to and/or during transluminal delivery.

The frame 200 provides a sufficiently rigid structure so that the valve component 100 can be anchored thereto and is capable of maintaining its desired configuration. The frame 200 also provides the mechanism by which the prosthetic valve device 1000 is retained in the proper position and orientation at the desired implantation site. The prosthetic valve device 1000 may be retained in the proper position and orientation at the desired implantation site by any known means known in the art, none of which are to be considered limiting of the present invention unless specifically recited in the claims. For example, the frame 200 may be anchored directly to the inner wall of the body lumen (or to a secondary frame or stent in which the prosthetic valve device 1000 is positioned). Such anchoring can be achieved, for example, via known techniques, including without limitation, suturing, stapling, puncturing, clamping or combinations thereof. In the exemplified embodiment, the frame 200 is a self-retaining structure that utilizes its tendency to diametrically expand to a diameter greater than the diameter of the body lumen at the implantation site, thereby creating a compression fit between the prosthetic valve device 1000 and the body lumen to retain the prosthetic valve device 1000 in place at the implantation site. The tendency of the frame 200 to diametrically expand can be achieved by forming the frame 200 out of a shape memory material. In some embodiments, the frame 200 is formed of nickel titanium. Other shape memory materials can be utilized in other self-retaining embodiments. In embodiments wherein the frame 200 is not a self-retaining structure, the frame can be constructed of any biocompatible material that is sufficiently rigid to provide the required support to the valve component 100. Suitable alternate materials include, without limitation, polymers, platinum, stainless steel, chonichrom, or combinations thereof.

The frame 200 comprises a tubular body 201 having an inner surface 202 and an outer surface 203. The tubular body 200 comprises a central axis (which is coincident with the axis A-A of the fluid passageway of the valve component 100). The tubular body 201 has a height $H_F$ measured from a bottom edge 204 of the tubular body 201 to a top edge 205 of the tubular body 201 along the axis A-A. The tubular body 201 further comprises an outer diameter $D_F$.

In the exemplified embodiment, the frame 200 is of the self-retaining type and thus, the outer diameter $D_F$ is selected so as to be larger than the diameter of the body lumen at implantation site. The height $H_F$, in one embodiment, is substantially equal to the outer diameter $D_F$ when in the implanted state. In one specific embodiment in which the prosthetic valve device 1000 is designed for implantation to replace an aortic valve, the outer diameter $D_F$ of the tubular body 201, pre-implant, is between 1 mm to 4 mm larger than the aortic annulus (which is the implantation site). In some embodiments, the aortic annulus is assumed to have a mean diameter of 22 mm in an elderly population and, thus, the outer diameter $D_F$ of the tubular body 201 is between 23 mm to 24 mm. In this exemplary embodiment, the height $H_F$ was also selected to be between 20 mm to 22 mm, and specifically approximately 21 mm. The invention, however, is in no way limited to any specific dimensions of the frame 200, either empirical or relative, unless specifically recited in the claims.

As mentioned above, the frame 200, and thus the tubular body 201, is sufficiently rigid and robust to withstand the forces resulting from the pressures imparted to the tubular body 201 by the valve component 100 during pro-longed operation of the prosthetic valve device 1000, whilst still firmly anchored at the implantation site. Thus, in one embodiment of the frame 200 wherein the tubular body 201 is formed of nickel titanium, the tubular body 201 has a thickness between 0.3 mm to 0.5 mm, with a thickness of 0.4 mm being selected in one specific embodiment. In other embodiments, depending on such factors as the material of construction of the tubular body 201, the dimensions of the tubular body 201, and the parameters of the implantation site, the thickness of the tubular body 201 will be adjusted accordingly.

The inner surface 202 of the tubular body 201 forms a cavity 206 that is open at both the top and bottom edges 204, 205, thereby forming an axial passageway. When the prosthetic valve device 1000 is fully assembled, the valve component 100 is disposed within the cavity 206 and anchored to the tubular body 201 (described in greater detail below).

In the exemplified embodiment, the tubular body 200 has a circular transverse cross-sectional profile. However, in alternate embodiments, the transverse cross-sectional profile of the tubular body 201 can take on other shapes. Noncircular transverse cross-sectional profiles may be desirable in instances wherein the frame is to be positioned within an outer stent component.

The tubular body 201 of the frame 200 comprises a plurality of posts 207 and a plurality of lattice structures 208 circumferentially extending between and connected to the posts 207. The posts 207 extend from the bottom edge 204 to the top edge 205 of the tubular body 201 and, in the exemplified embodiment are substantially linear structures that are substantially parallel to the axis A-A. The posts 207 are arranged about the circumference of the tubular body 201 in a spaced-apart manner. More specifically, the posts 207 are arranged in an equi-spaced manner about the circumference of the tubular body 201. In certain embodiments, the number of posts 207 will correspond with the number of commissures 115 present on the valve component 100 because the posts 207 provide structures within the tubular body 201 to which the commissures 115 are mounted. The tubular body 201 comprises a post 207 for each commissure 115 of the valve component 100. The posts 207 are circumferentially arranged about the circumference of the tubular body 201 so as to be radially aligned with the commissures 115 of the valve component 100.

In the exemplified embodiment, there are three posts 207 because the valve component 100 is a tricuspid type valve, thereby having three commissures 115. However, in alternate embodiments, the tubular body 201 can include more or less than three posts 207 as desired. Moreover, in certain embodiments, it is possible that the number of posts 207 can be greater than the number of commissures 115 of the valve component 100 in an effort to increase axial rigidity of the frame 200.

As mentioned above, the tubular body 201 of the frame comprises lattice structures 208 that extend between each of the posts 207. In the exemplified embodiment, the lattice structures 208 and the posts 207 are integrally formed as a unitary structure free of seams. Thus, the tubular body 201 is a unitary structure. In some embodiments, the tubular body 200 may be made from wire or may be laser cut from a tube, sheath, or the like. One preferred method of forming the tubular body 200 is described below with respect to FIGS. 12-14.

Figure 8:
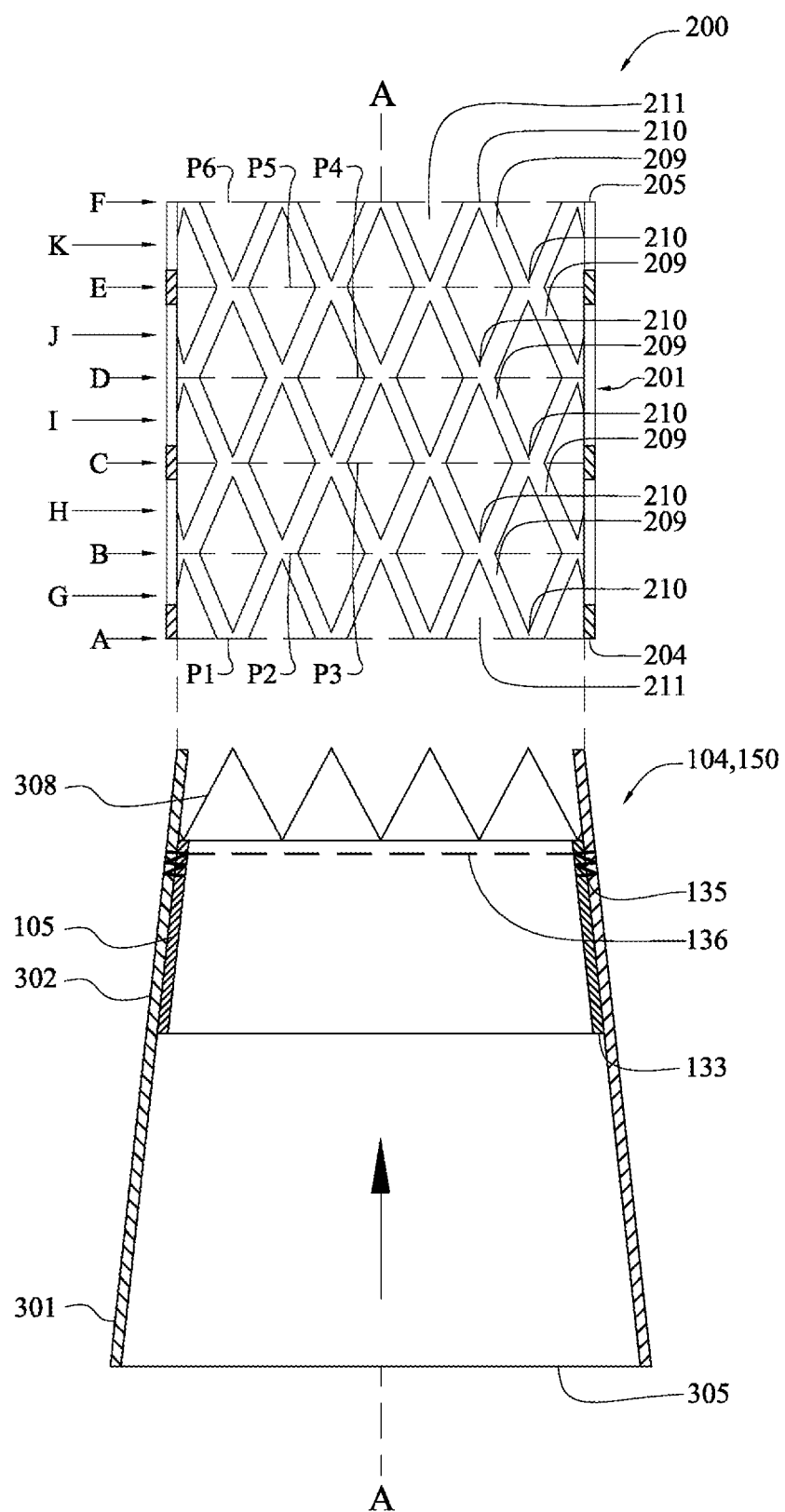
FIG. 8 is an axial cross-sectional schematic of the annular sleeve of FIG. 7 positioned in axial alignment for anchoring to the frame of the prosthetic valve device of FIG. 1, according to some embodiments of the present invention.

Referring now to FIGS. 1 and 8 concurrently, each of the lattice structures 208 comprise struts 209 that intersect at nodes 210. The struts 209 provide structures to which the valve component 100 can be anchored to the tubular body 201 of the frame 200. The nodes 210 are arranged in a plurality of circumferentially extending rows A-F that are axially spaced from one another (see FIG. 8). The nodes 210 within each circumferential row A-F lie in the same transverse plane as other nodes 210 within that same circumferential row A-F. These transverse reference planes are denoted as dotted lines P1-P6. As a result of the aforementioned geometrical arrangement of the rows of the nodes 210 within the lattice structures 208, the struts 209 are also arranged in circumferential rows G-K, wherein the circumferential rows G-K of the struts 209 are defined between the transverse planes A-F. In the exemplified embodiment, there are six circumferential rows A-F of nodes 210 and five circumferential rows G-K of struts 209. In other embodiments, more or less circumferential rows A-F of nodes 210 and/or circumferential rows G-K of struts 209 can be used. The struts 209 within each of the circumferential rows G-K are oriented so as to form a saw-tooth configuration. The aforementioned configuration of the lattice structures 208 of the tubular body 201 is used to anchor the valve component 100 within the frame 200 in a manner that prevents both axial and circumferential slippage of the valve component 100 during operation of the prosthetic valve device 1000.

The lattice structures 208 further comprise a plurality of open cells 211 formed by the struts 210. In the exemplified embodiment, all of the open cells 211 within all of the lattice structures 208 are a diamond-shape or a partial diamond-shape. The invention, however, is not so limited in all embodiments.

Referring now to FIGS. 1-4 and 10 concurrently, the valve component 100 will be discussed in greater detail. The valve component 100 comprises a fluid passageway 101 having an axis A-A through which a bodily fluid can flow. The valve component 100 is the working component of the prosthetic valve device 1000 and is alterable between: (1) an open state, shown in FIG. 4, in which the fluid passageway 101 is open and allows a body fluid to pass therethrough from the fluid inlet 102 to the fluid outlet 103; and (2) a sealed state, shown in FIG. 2, in which the fluid passageway 101 is sealed and prevents backflow of bodily fluid that has exited the fluid outlet 103. The valve component 100 is disposed within and anchored to the tubular body 201 of the frame 200 so as to be capable of repetitively alternating between the open and closed states when the prosthetic valve device 1000 is anchored at the implantation site.

The valve component 100 generally comprises an annular sleeve 104, an annular belt 105 and a plurality of commissure strips 106. Each of the annular sleeve 104, the annular belt 105 and the plurality of commissure strips 106 are preferably formed of a pliable material. In some embodiments, each of the annular sleeve 104, the annular belt 105 and the plurality of commissure strips 106 are formed of the same material. However, in alternate embodiments, the annular sleeve 104, the annular belt 105 or the plurality of commissure strips 106 may be formed of different pliable or non-pliable materials with respect to one or both of the others. Suitable materials for construction of the annular sleeve 104, the annular belt 105 and/or the plurality of commissure strips 106 include, without limitation, biological tissues and biocompatible polymers. Suitable biological tissues may include tissues that are human and/or porcine in nature. In one specific embodiment, the annular sleeve 104, the annular belt 105 and the plurality of commissure strips 106 are formed of porcine pericardium tissue that is suitably treated for biocompatibility and/or to prevent decay. Suitable biocompatible polymers include, without limitation, polyurethane, silicones, or combinations thereof.

The annular sleeve 104 generally comprises an annular inner wall 107 and an annular cuff 108 (described in greater detail below). The valve component 100 extends from an inlet edge 109 to an outlet edge 110 when assembled for use in the prosthetic valve device 1000. The inlet edge 109 defines the fluid inlet 102, which in the exemplified embodiment is an opening lying within a transverse plane. The outlet edge 110 defines the fluid outlet 103, which in the exemplified embodiment is an opening lying within a transverse plane. The annular sleeve 104 comprises both the inlet edge 109 and the outlet edge 110. The annular inner wall 107 of the annular sleeve 104 extends from the inlet edge 109 to the outlet edge 110 and defines the fluid passageway 101 that extends between the fluid inlet 102 and the fluid outlet 103. The annular inner wall 107 of the annular sleeve 104 extends a height $H_S$ measured along the axis A-A from the fluid inlet 102 to the fluid outlet 103. Conceptually, the height $H_S$ can also be considered as defining the height of the annular sleeve 104 when the valve component 100 is fully formed, or the height of the fluid passageway 101.

In the exemplified embodiment, the annular inner wall 107 of the annular sleeve 104 defines the fluid passageway 101. More specifically, the inner surface 111 of the annular inner wall 107 forms the fluid passageway 101. The fluid passageway 101 extends along the axis A-A and forms a conduit through the cavity 206 of the tubular body 201 of the frame when the prosthetic valve device 1000 is assembled.

The valve component 100 comprises a plurality of commissures 115 arranged about the circumference of the outlet edge 110 in a spaced-apart manner. As discussed in greater detail below, the commissures 115 are anchored to the tubular body 201 of the frame 200. The commissures 115 are equi-spaced from one another about the circumference of the outlet edge 110. In the exemplified embodiment, three commissures 115 are provided and are arranged approximately 120° apart about the circumference of the outlet edge 110. In alternate embodiments, more or less than three commissures 115 can be formed.

During operation of the prosthetic valve device 1000 at the implantation site, the commissures 115 act as anchoring points for the annular inner wall 107 along the outlet edge 110. Because the annular sleeve 104 (and thus the annular inner wall 107) is formed of a pliable material, the commissures 115 form a plurality of collapsible leaflets 112-114 therebetween. The collapsible leaflets 112-114 are circumferential sections of the annular inner wall 107 of the annular sleeve 104. One of the commissures 115 is located between each pair of adjacent collapsible leaflets 112-114. The collapsible leaflets 112-114 collectively form the fluid outlet 103 (during the open-state of the valve component 100). During the pumping of bodily fluid through the fluid passageway 101 (from the fluid inlet 102 to the fluid outlet 103), the collapsible leaflets 112-114 are deflected from their closed-state (FIG. 2) to their open-state (FIG. 4), thereby allowing the bodily fluid to flow through the fluid passageway 101 and out of the prosthetic valve device 1000. Once pressure on the fluid inlet 102 is ceased, the collapsible leaflets 112-114 collapse in upon themselves and transition from their open-state (FIG. 4) to their closed-state (FIG. 2), thereby prohibiting bodily fluid that has exited the fluid outlet 103 from back-flowing into the fluid passageway 101.

Referring now to FIGS. 1-3 and 11A-B concurrently, the commissures 115 are formed by commissure strips 106 that are affixed to the outlet edge 110 of the annular inner wall 107 at the desired circumferential location. Thus, similar to the commissures 115, the commissure strips 106 are arranged about the circumference of the outlet edge 110 in an equi-spaced circumferential manner. In the exemplified embodiment, each of the commissures 115 is formed by cinching a portion 116 of the annular inner wall 107 of the annular sleeve 104 between opposing legs 117A-B of one of the commissure strips 106. In the exemplified embodiment, each commissure strip 106 is an elongated strip of material that is folded over the outlet edge 110 of the cinched portion 116, thereby forming a general U-shape (best shown in FIG. 11A). Thus, in such an embodiment, each commissure strip 106 comprises the opposing legs 117A-B and a bight portion 118. However, in alternate embodiments, each of the opposing legs 117A-B of the commissure strips 106 can be formed by two separate strips of material that are positioned on opposing sides of the cinched portion 116 and affixed thereto. In certain other alternate embodiments, the commissure strips 106 can be formed out of a properly dimensioned portions of the annular sleeve 104 itself, rather than as separate components.

Once the cinched portions 116 of the annular inner wall 107 are disposed between the opposing legs 117A-B of the commissure strips 106, the commisure strips 106 are affixed to the annular inner wall 107 of the annular sleeve 104. When so positioned, both of the opposing legs 117A-B of each commissure strip 106 are adjacent to an outer surface 119 of the annular inner wall 107 at the cinched portion 116. More specifically, as exemplified, the inner surfaces 121 of the opposing legs 117A-B of the commissure strips 106 are in surface contact with the outer surface 119 of the annular inner wall 107 at the cinched portions 116.

For each commissure 115, the opposing legs 117A-B of the commissure strip 106 and the cinched portion 116 of the annular inner wall 107 collectively form a multi-layer structure 120. In the exemplified embodiment, each multi-layer structure 120 includes four layers, a first layer formed by the leg 117A of the commissure strip 106, second and third layers formed by the cinched portion 116 of the annular inner wall 107 of the annular sleeve 104, and a fourth layer formed by the leg 117B of the commissure strip 106. At least one fastening element 122 penetrates through each layer of the multi-layer structure 120 so as to affix the opposing legs 117A-B of the commissure strip 106 and the cinched portion 116 of the annular inner wall 107 together. As used herein, the terms "fastening element" and "fasteners" are interchangeable. In the exemplified embodiment, the fastening element 122 is a single suture. However, in alternate embodiments, the fastening element 122 can be multiple sutures, or can be other structures such as staples, adhesives, barbs, clamps or combinations thereof.

The suture 122, in the exemplified embodiment, comprises free ends 123, 124 that extend from the opposing sides of the commissure 115. During assembly of the prosthetic valve device 1000, these free ends 123, 124 are used to anchor the commissure 115 to the tubular body 201 of the frame. For example, in one embodiment, for each commissure 115, the free ends 123, 124 of each suture 122 are wrapped around the axial post 207 of the frame 200 with which that commissure 115 is radially aligned. For each commisure 115, the commisure strip 106 is affixed to the cinched portion 116 so that a cusp portion 125 protrudes radially outward from the commissure strip 106. The cusp portions 125 are anchored to the tubular body 201 of the frame 200 to anchor the commisures 115 in place. In the exemplified embodiment, each of the cusp portions 125 is anchored to a corresponding axial post 207 of the tubular body 201 that is in radial alignment with that commissure 115. The anchoring of each cusp portion 125 is achieved by a plurality of sutures 126 that wrap around the axial post 207 so as to retain both the axial and circumferential position of the corresponding commissure 115 with respect to the frame 200. When the valve component 100 is anchored to the frame 200 to form the prosthetic valve device 1000 (as shown in FIG. 1), the cusp portions 125 are located radially inward of the tubular body 201 of the frame 200. In other embodiments, the cusp portions 125 can be anchored utilizing different fasteners, such as staples, adhesives, clamps, barbs, or combinations thereof.

As a result of using the commissure strips 106, the commissures 115 are formed as post-like structures. Moreover, in one specific embodiment, because the commissures 115 are formed entirely out of the pliable material (which in the exemplified embodiment is the cinched portion 116 and the commissures strips 106), the commissures 115 allow for some movement, similar to those in the native aortic valve.

Figure 7:
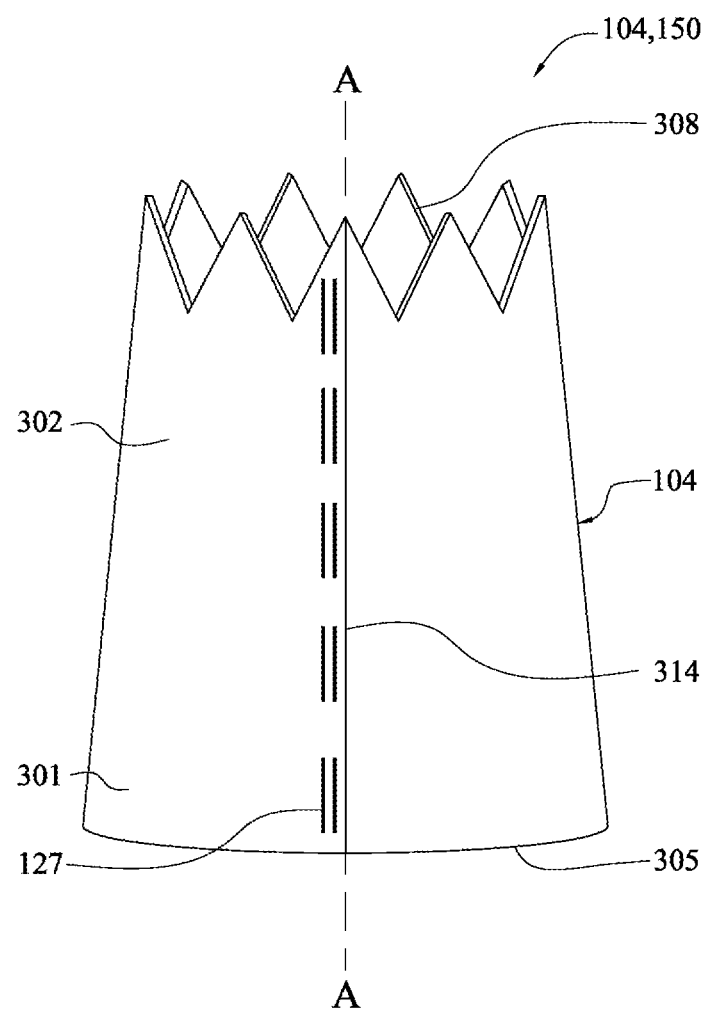
FIG. 7 is a perspective of the leaflet blank of FIG. 6 formed into an annular sleeve, according to some embodiments of the present invention.

Moreover as will be described in greater detail below, the annular sleeve 104, in certain embodiments, will be formed by a single rolled sheet of material having a single axial seam 127 (FIG. 7). In such an embodiment, when the annular sleeve 104 is formed to create the annular inner wall 107, this single axial seam 127 can be located within one of the cusp portions 125. Locating the axial seam 107 within one of the cusp portions 125 prevents the axial seam 127 from being located on, and potentially affecting the operation of, the leaflets 112-114. In embodiments wherein the annular sleeve 104 (and thus the annular inner wall 107) are formed by multiple sheets of material connected together via multiple axial seams 127, it may be preferred that all of such axial seams 127 be located within the cusp portions 125. The invention, however, is not so limited in all embodiments. In some embodiments, the sutures used herein are a 4-0 Ethicon nylon black monofilament, for example, in certain embodiments. Other sutures may also be used. For example, one other suture type is 5-0 Ethibond.

Utilization of the commissure strips 106 to form the commissures 115 allows the leaflets 112-114 to be formed free of both affixing and anchoring penetrations. All such affixing and anchoring penetrations in the upper portion of the annular inner wall 107 are located within the commissures 115, and specifically within the commissure strips 106, the cinched portions 116, and/or the cusp portions 125. Thus, the commissure strips 106 help protect the valve component 100 from failure/fatigue at the aforementioned affixing and anchoring penetrations by isolating them from the working motion of the collapsible leaflets 112-114. It should be noted that in certain embodiments, the commissures 115 can be formed in a different manner than utilizing the commissure strips 106.

Further, the commissure strips 106 themselves are designed to prevent damage to the collapsible leaflets 112-114. Specifically, each of the opposing legs 117A-B of the commissure strips 106 comprises an inner edge 128. Each of the inner edges 128 have a bottom portion 129 that tapers radially outward. Preferably, all corners of the opposing legs 117A-B of each commissure strip 106 are rounded.

Figure 10:
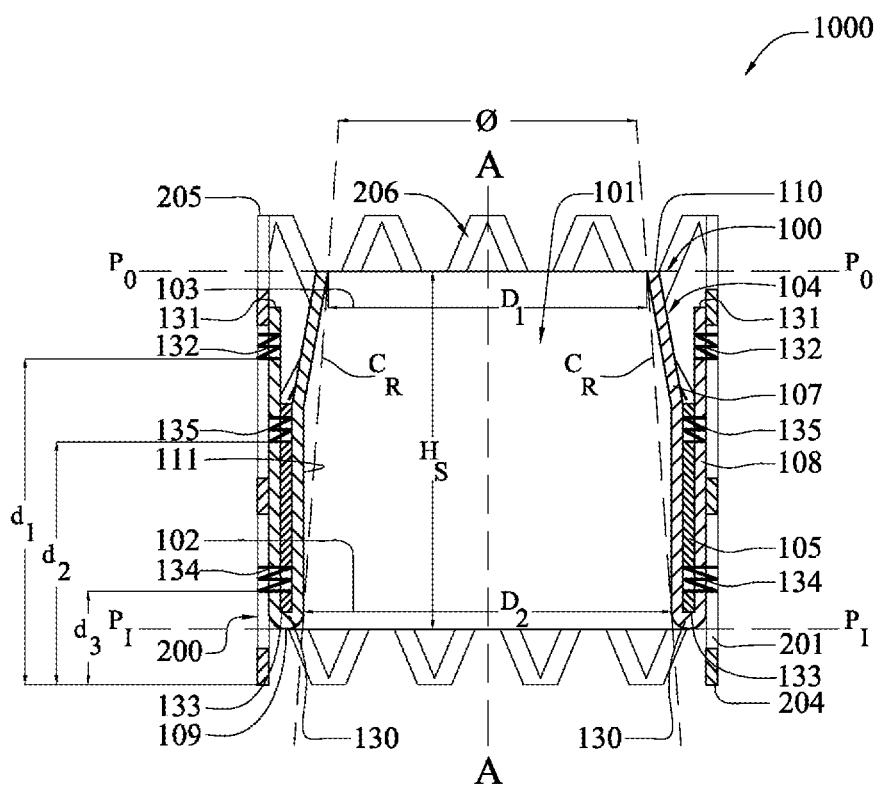
FIG. 10 is an axial cross-sectional schematic of the assembly of FIG. 8, wherein the annular sleeve has been folded-in on itself, and in which commissures have been created anchoring an outlet edge of the annular sleeve to the frame.
Figure 11A:
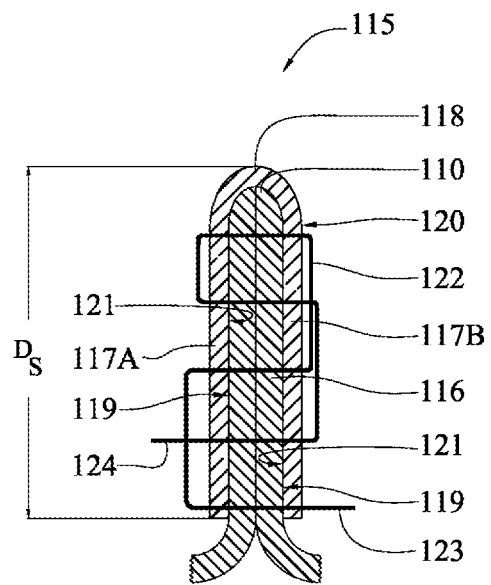
FIG. 11A is an axial cross-sectional schematic of one of the commissures of the prosthetic valve device of FIG. 1 according to some embodiments of the present invention.
Figure 11B:
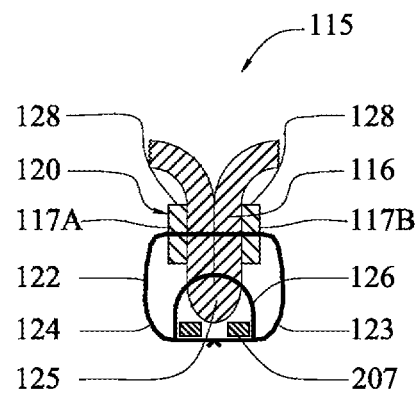
FIG. 11B is a transverse cross-sectional schematic of one of the commissures of the prosthetic valve device of FIG. 1 according to some embodiments of the present invention.

Referring to FIGS. 10 and 11 concurrently, when the commissure strips 106 are affixed to the annular inner wall 107, the opposing legs 117A-B of each commissure strip 106 extend an axial distance $D_S$ from the outlet edge 110 toward the inlet edge 109 of the annular inner wall 107. The axial distance $D_S$ is less than the axial height $H_S$ of the annular inner wall 107, which is measured from the inlet edge 109 to the outlet edge 110 along the axis A-A. In certain embodiments, the axial distance $D_S$ is 30% to 55% of the axial height $H_S$. In one specific embodiment, the axial distance $D_S$ is between 5 to 7 mm, and more preferably approximately 6 mm. The axial height $H_S$, in such an embodiment, can be between 13 to 15 mm, and more preferably approximately 14 mm.

Figure 2:
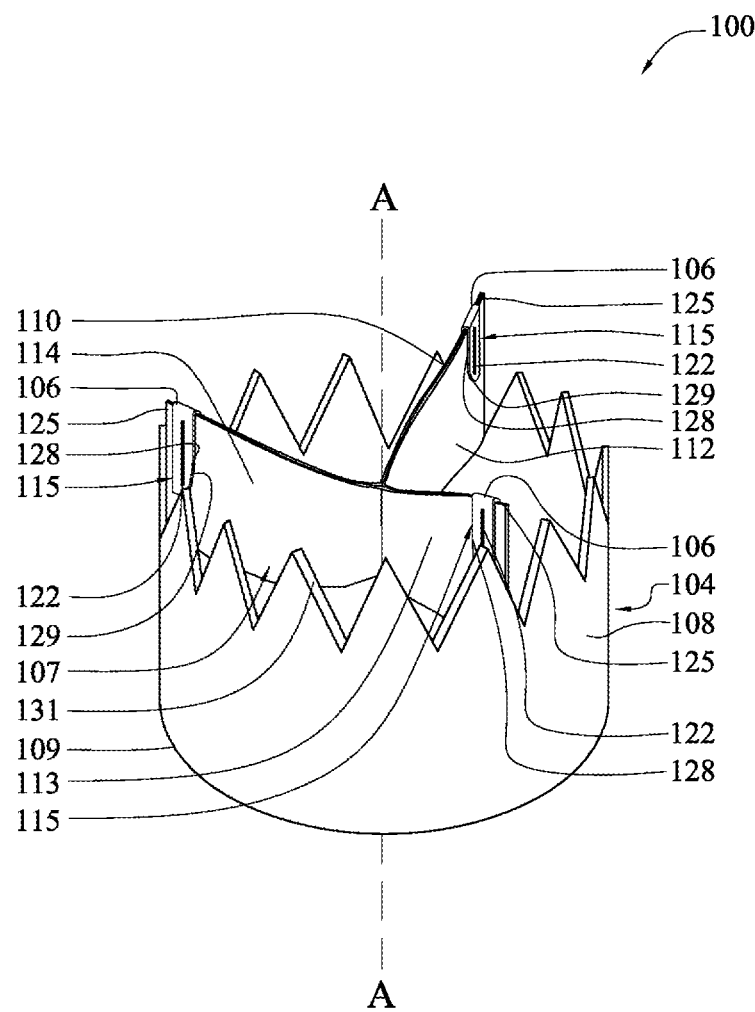
FIG. 2 is a perspective view of the valve component of the prosthetic valve device removed from the frame, and in a closed state, according to some embodiments of the present invention.
Figure 4:
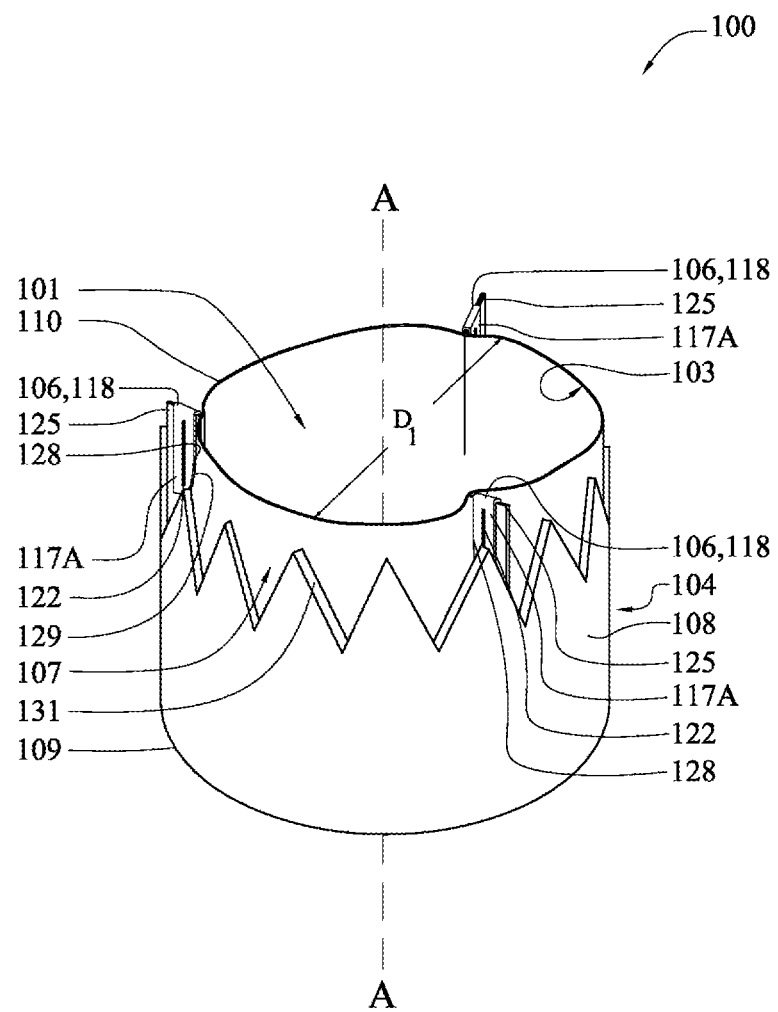
FIG. 4 is a perspective view of the valve component of the prosthetic valve device removed from the frame, and in an open state, according to some embodiments of the present invention.

Referring solely now to FIGS. 4 and 10 concurrently, optimization of the design of the valve component 100, in one embodiment of the invention, will be discussed. FIG. 10 is an axial cross-sectional view of the fully assembled prosthetic valve device 1000 of FIG. 1, in the open-state. The valve component 100 is disposed within the cavity 206 of the frame 200 and anchored to the tubular body 201 of the frame 200 (the anchoring of which was partially discussed above and will be described in greater detail below). The dimensions of the valve component 100 (and especially the annular sleeve 104 and/or the commissures 115) are optimized so that the leaflets 112-114 achieve: (1) no leakage of the bodily fluid through the fluid passageway 101 when the leaflets 112-114 are in the closed-state (FIG. 2); (2) synchronous closure of the leaflets 112-114; (3) symmetric closure of the leaflets 112-114; and (4) minimization or elimination of folds in the leaflets 112-114 (in both the open-state and closed-state).

As mentioned above, the inner surface 111 of the annular inner wall 107 defines the fluid passageway 101 which extends along the axis A-A. The fluid inlet 102, which is defined by the inlet edge 109, conceptually defines an opening having a second diameter $D_2$ and that lies within a transverse plane $P_1$ (visible as a line in FIG. 10). Similarly, the fluid outlet 103, which is defined by the outlet edge 110 (excluding the cinched portions 116), conceptually defines an opening having a first diameter $D_1$ and that lies within a transverse plane $P_0$ (visible as a line in FIG. 10). The second diameter $D_2$ is greater than the first diameter $D_1$. In some embodiments, the annular sleeve 104 is dimensioned so that the second diameter $D_2$ is in a range of 19 to 21 mm, with 20.25 mm being preferred in one specific embodiment, while the first diameter $D_1$ is in a range of 15 to 17 mm, with 16.25 mm being preferred in one specific embodiment. The invention, however, is not limited to any specific measurements unless specifically recited in the claims. Moreover, as will become apparent from the discussion below, the empirical numbers of the optimization dimensions is not as important as the relativity between said dimensions, which can be scaled up or down as necessary.

The transverse plane $P_1$ is substantially parallel to the transverse plane $P_0$ in the exemplified embodiment, and separated by the height $H_S$ (which can also be considered the height of the annular inner wall 107 and the length of the fluid passageway 101). Conceptually, the fluid inlet 102 and the fluid outlet 103 can be considered to form a reference truncated cone $C_R$, wherein the fluid inlet 102 forms the delimiting lower plane of the reference truncated cone $C_R$ while the fluid outlet 103 forms the delimiting upper plane of the reference truncated cone $C_R$. In FIG. 10, the reference truncated cone $C_R$ has a central axis that is coincident with the axis A-A, and is simply illustrated as the dotted lines $C_R$ due to the plan-nature of FIG. 10. The reference truncated cone $C_R$ is a portion of cone having an angle $\Theta$. In certain embodiments, the angle $\Theta$ is in a range of 9° to 11°, and in one specific embodiment, the angle $\Theta$ is approximately 10°.

Furthermore, it has been discovered that, in certain embodiments of the invention, optimal performance of the valve component 100 is achieved when: (1) the angle $\Theta$ is in a range of 9° to 11°; and (2) the second diameter $D_2$ and the height $H_S$ are selected so that the ratio of the second diameter $D_2$ to the height $H_S$ is in a range of 1.3:1 to 1.5:1. In one specific embodiment, optimal performance of the valve component 100 is achieved when: (1) the angle $\Theta$ is approximately 10°; and (2) the ratio of the second diameter $D_2$ to the height $H_S$ is approximately 1.4:1. Utilizing the preferred angle $\Theta$ and the preferred ratio of the second diameter $D_2$ to the height $H_S$ allow the valve component 100 to be scaled up or down as desires while still achieving optimal performance. The frame 200 can similarly be scaled up or down in a corresponding manner to accommodate the scale of the valve component 100.

Figure 3:
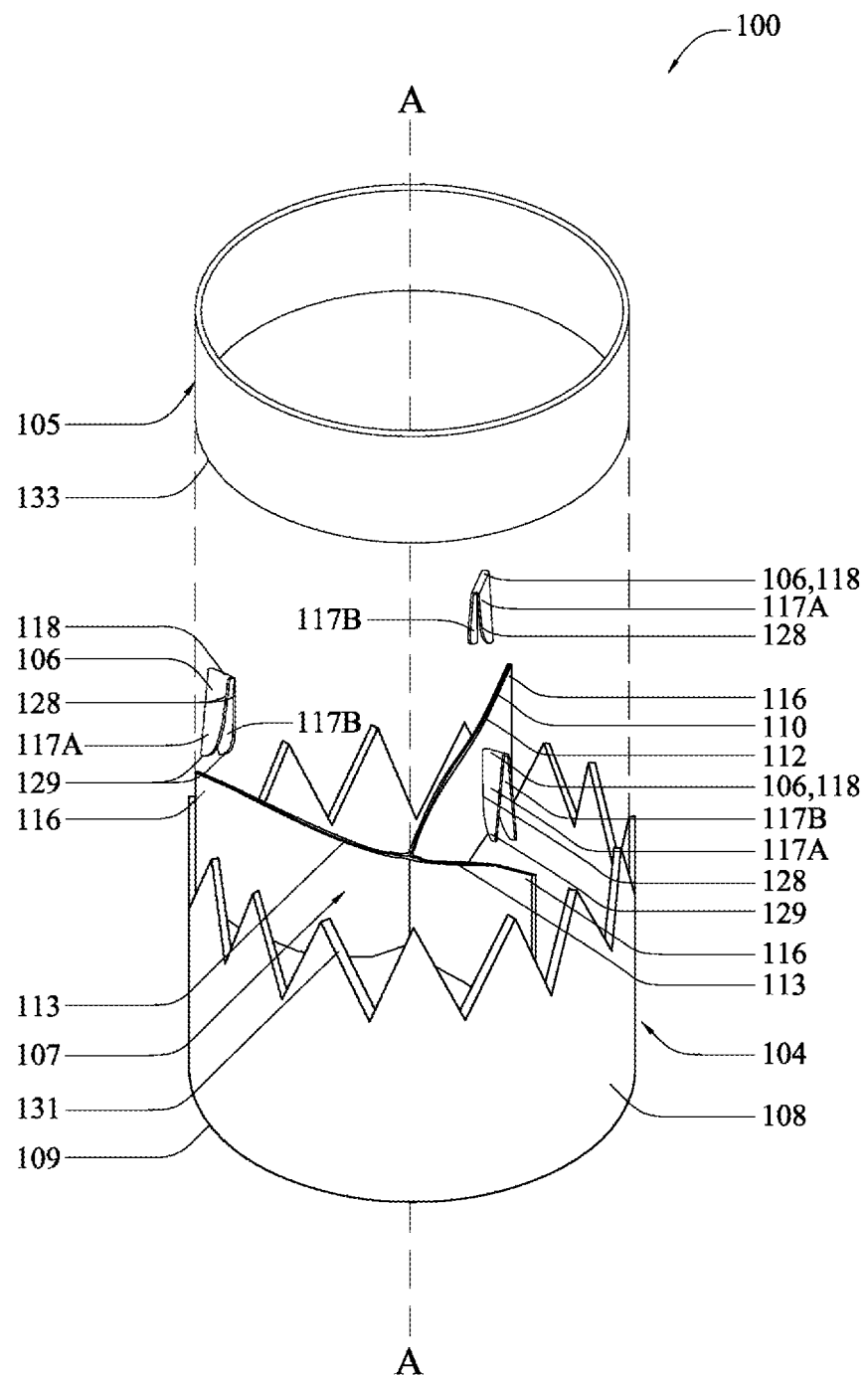
FIG. 3 is an exploded view of the valve component of FIG. 2.

Referring now to FIGS. 3 and 10 concurrently, the structure of the valve component 100 will be further discussed in relation to the annular belt 105 and the annular cuff 108. The annular sleeve 104 comprises the annular inner wall 107 and the annular cuff 108. In the exemplified embodiment, the annular sleeve 104 is formed from single sheet of material and, thus, the annular inner wall 107 and the annular cuff 108 are also integral with one another. However, in alternate embodiments, it is possible that the annular inner wall 107 and the annular cuff 108 can be separate sheets of material that are coupled together.

The annular cuff 108 and annular inner wall 107 are formed by folding the annular sleeve 104 over at the inlet edge 109, thereby forming a bight portion 130. Thus, the bight portion 130 comprises (or forms) the inlet edge 109 and can conceptually considered as defining the fluid inlet 102. The annular cuff 108 is concentric to and circumferentially surrounds the annular inner wall 107. In the exemplified embodiment, both the annular cuff 108 and the annular inner wall 107 are generally concentric to the axis A-A. Further, in the exemplified embodiment, the annular cuff 108 is a single continuous ring-like element. It is possible, in certain alternate embodiments, that the annular cuff 108 can be formed by a collection of non-continuous segments.

The annular cuff 108 extends axially from the inlet edge 109 toward the outlet edge 110, terminating at a top edge 131. As discussed in greater detail below, the top edge 131 of the annular cuff 108 is anchored to the tubular body 201 of the frame 200. In the exemplified embodiment, the top edge 131 is located below the top edge 205 of the tubular body 201 of the frame 200 when the prosthetic valve device 1000 is assembled. The top edge 131 of the annular cuff 108 is saw-toothed in the exemplified embodiment. The saw-tooth pattern of the top edge 131 is configured to correspond to the lattice structures 208 of the tubular body 201 of the frame 200 so as to facilitate anchoring thereto. More specifically, the saw-tooth pattern of the top edge 131 is configured to correspond to the configuration of the struts 209 of the lattice structures 208 that make up the circumferential row J (FIG. 8). Once the saw-toothed top edge 131 of the annular cuff 208 is aligned with the struts 209 of the lattice structures 208 of circumferential row J (as shown in FIG. 1), the saw-toothed top edge 131 is anchored thereto via fasteners, such as the sutures 132 (which are all located in circumferential row J). In other embodiments, the anchoring of the top edge 131 of the annular cuff 208 can be achieved via staples, barbs, clamps, adhesives, fusing, or combinations thereof. Furthermore, in alternate embodiments, the top edge 131 may take on a configuration other than saw-tooth, such as linear, contoured, sine-wave, irregular shape, or combinations thereof.

The annular belt 105 is formed of a single widened strip of sheet material that is concentric to and circumferentially surrounds the annular inner wall 107. The annular belt 105 is positioned between the annular cuff 108 and the annular inner wall 107. The annular cuff 108 is positioned so that a bottom edge 133 of the annular cuff 108 is adjacent to the bight portion 130 of the annular sleeve 104. During operation of the valve component 100 during implantation, the bottom edge 133 of the annular cuff 108 acts as a circumferential barrier that prevents stresses and strains experienced by the annular inner wall 107 (due to fluid flow and movement of the collapsible leaflets 112-114) from being imparted to the anchoring penetrations in the annular sleeve 104 resulting from the fasteners 134 that anchor the inlet portion of the valve component 100 to the tubular body 201 of the frame 200. In the exemplified embodiment, the fasteners are 134 are sutures. As exemplified, the sutures 134 are run in a saw-tooth configuration along the struts 209 of circumferential row H. In other embodiments, the anchoring of the inlet portion of the valve component 100 can be achieved via staples, barbs, clamps, adhesives, fusing, or combinations thereof.

Figure 6:
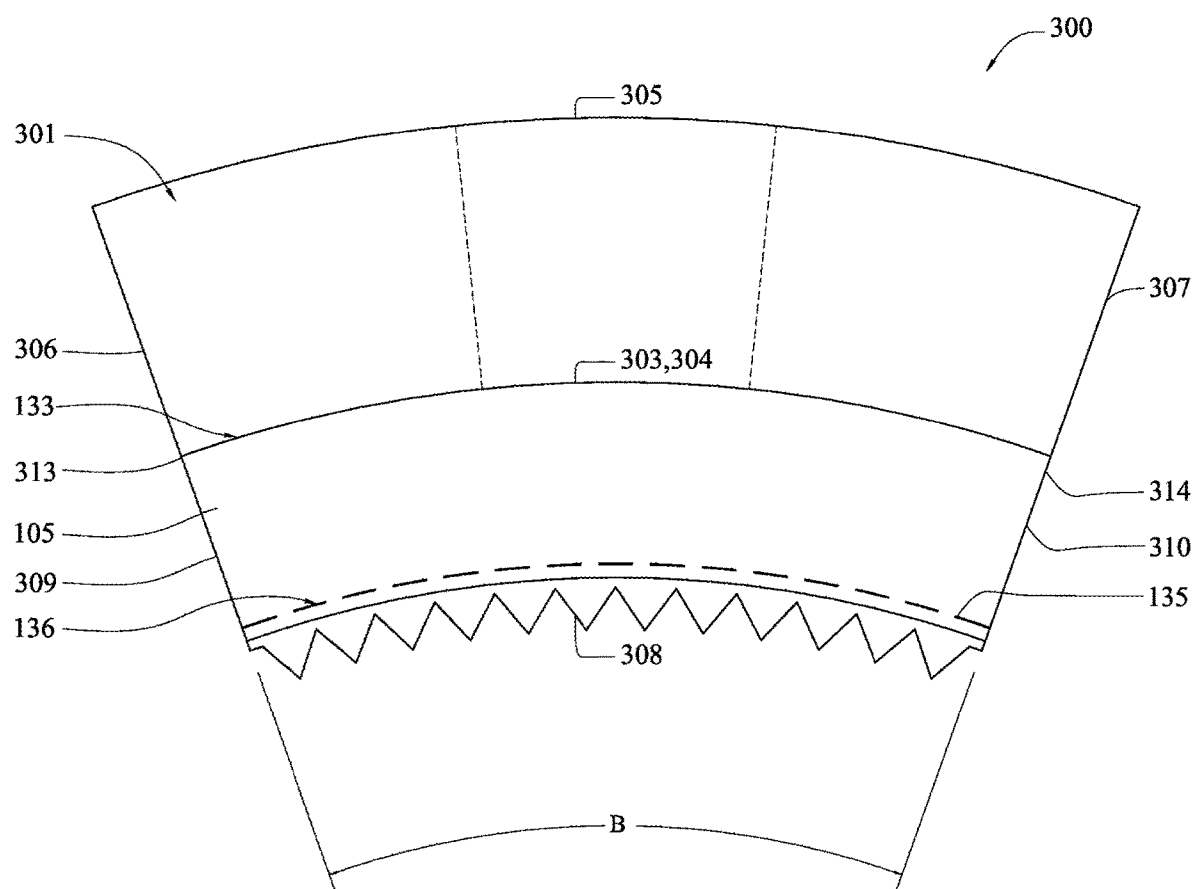
FIG. 6 is a plan view of the leaflet blank of FIG. 5 with a belt affixed thereto, according to some embodiments of the present invention.

Referring now to FIGS. 1 and 10 concurrently, the annular belt 105 is affixed to the annular sleeve 104 only along the annular cuff 108. As a result, there are no penetrations in the annular inner wall 107 resulting from the attachment of the annular belt 105 to the annular sleeve 104. In the exemplified embodiment, the annular belt 105 is circumferentially affixed to the annular cuff 108 at two axial locations, the first of which is formed by the fasteners 134 and the second of which is formed by the fasteners 135. The fasteners 135, in the exemplified embodiment are sutures, arranged in a straight circumferential seam 136 (FIG. 6).

The fasteners 135 merely affix the annular belt 105 to the annular cuff 108. The fasteners 134, however, are also used to anchor the inlet portion of the valve component 100 to the tubular body 201 of the frame 200. Thus, the inlet portion of the valve component 100 is anchored to the tubular body 201 of the frame 200 by penetrating only the annular cuff 108 and the annular belt 105. Furthermore, because the outlet portion of the valve component 100 is anchored to the tubular body 201 of the frame 200 only by way of the commissures 115 (described above), the annular inner wall 107 is free of anchoring penetrations from the inlet edge 109 to the commissures 115 at the outlet edge 110. In fact, the only penetrations in the annular inner wall 107 between the inlet edge 109 to the commissures 115 are the affixing penetrations that extend axially due to the existence of the single axial seam 127 (FIG. 7). However, these affixing penetrations present minimal risk of failure/wear due to their axial alignment and due to the fact that they are not located within the moving collapsible leaflets 112-114.

Thought of another way, the top edge 131 of the annular cuff 108 is anchored to the tubular body 201 via fasteners 132 at a first axial distance $d_1$ from a bottom edge 204 of the tubular body 201 of the frame 200. The top portion of the annular belt 105 is affixed to the annular cuff 108 at a second axial distance $d_2$ via fasteners 135 from the bottom edge 204 of the tubular body 201 of the frame 200. The bottom portion of the annular belt 105 is affixed to the annular cuff 108 and anchored to the tubular body 201 at a third axial distance $d_3$ via fasteners 134 from the bottom edge 204 of the tubular body 201 of the frame 200. The first axial distance $d_1$ is greater than the second axial distance $d_2$, and the second axial distance $d_2$ is greater than the third axial distance $d_3$. Isolation of the anchoring penetrations that anchor the inlet portion of the valve component 100 to the frame 200 from working stresses and strains is accomplished, in part, by anchoring the inlet portion of the annular sleeve 204 using only the annular cuff and only at an axial distance above the inlet edge 209.

In the exemplified embodiment, when the valve component 100 is anchored within the tubular body 201 of the frame 200, the inlet edge 109 is located at an axial location between the top edge 205 and the bottom edge 204 of the tubular body 201 of the frame 200. Thus, the annular cuff 108 is located within the tubular body 201 of the frame 200. However, in alternate embodiments, the annular cuff 108 may be folded over the bottom edge 204 of the tubular body 201 of the frame 200, thereby resulting in the inner annular wall 107 being located inside of the tubular body 201 of the frame 200 while the annular cuff 108 is located outside of the tubular body 201 of the frame 200. In such embodiments, the annular belt 105 can be located inside or outside of the tubular body 201 of the frame 200. However, in such embodiments, the annular belt 105 will be axially positioned so that the bottom edge 133 of the annular belt 105 extends beyond the bottom edge 204 of the frame 200. Such an arrangement allows the bottom edge 133 of the annular belt 105 to protect the annular sleeve 104 from being damaged by the bottom edge 204 of the frame 200 during operation and/or implantation. Moreover, positioning the annular cuff 108 outside of the tubular body 201 may result in a better seal between the prosthetic valve component 1000 and the walls of the body lumen at the implantation site.

As mentioned above, in the exemplified embodiment, the annular sleeve 104 comprises both the annular inner wall 107 and the annular cuff 108. However, in alternate embodiments, the annular cuff 108 may be omitted and the annular sleeve 104 may simply comprise the annular inner wall 107. In such alternate embodiments, the annular sleeve 104 itself would essentially take on the form of the annular inner wall 107 and form the fluid passageway 101 as discussed above.

Figure 5:
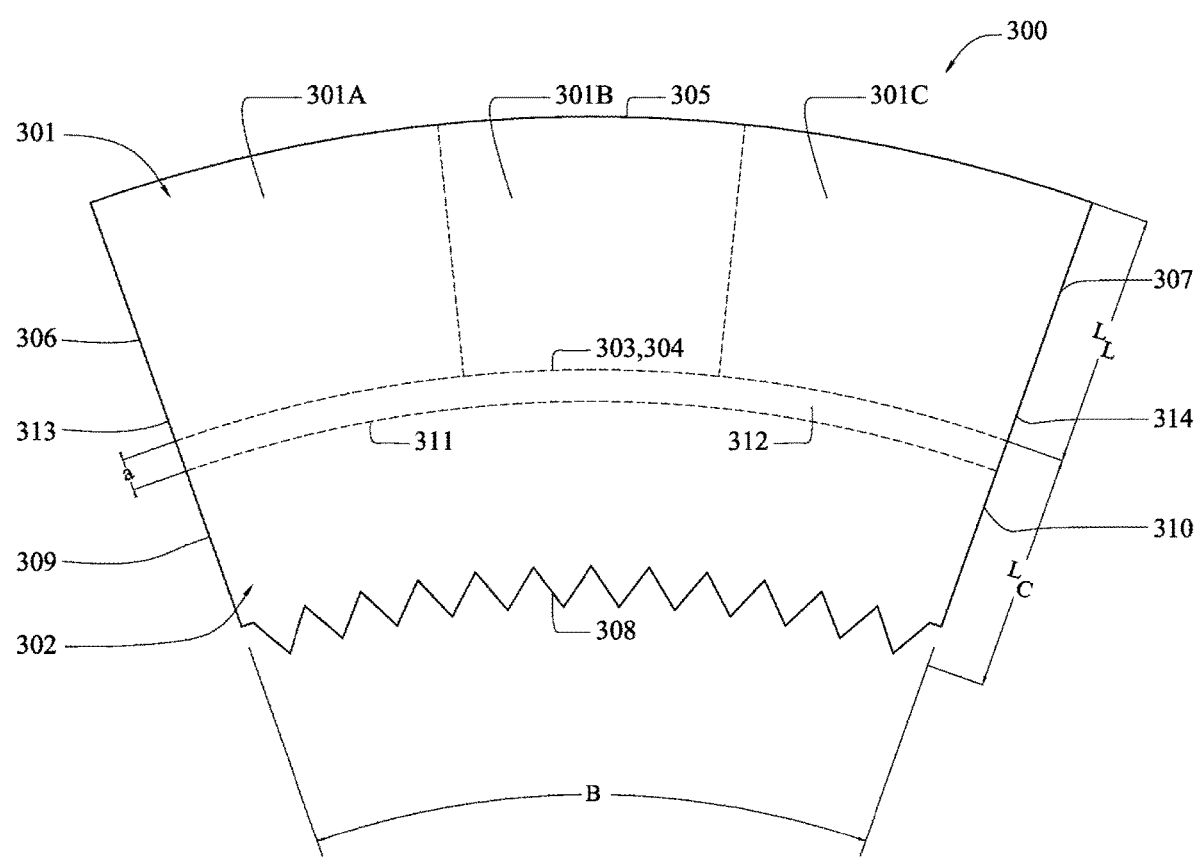
FIG. 5 is a plan view of leaflet blank according to some embodiments of the present invention.

Referring now to FIGS. 5-10, a method of forming the prosthetic valve device 1000 according to an embodiment of the present invention will be described. Referring first to FIG. 5, a blank 300 having the exemplified dimensions and geometry is cut (or otherwise formed) from a single sheet of pliable material, such as a sheet of natural tissue. Alternate materials could include sheets of pliable biocompatible polymers that could be formed to size and shape in flexible sheets or cut later to size and shape. The dimensions and geometry of the blank 300 are selected to achieve the optimal leaflet performance discussed.

The blank 300 generally comprises a leaflet section 301 and a cuff section 302. When folded and formed into the valve component 100, the leaflet section 301 will form the annular inner wall 107 while the cuff section 302 will form the annular cuff 208. The arcuate top edge 305 will form the outlet edge 110. With respect to the leaflet section 301, sub-sections 301A-C will form the collapsible leaflets 112-114 respectively. The leaflet section 301 is conceptually separated from the cuff section 302 by a fold line 303. The fold line 303 is the location at which the annular sleeve 104 will be folded upon itself to form the annular inner wall 307 and the annular cuff 108. Thus, the fold line 303 also demarcates the location at which the inlet edge 109 (and bight portion 130) will be formed in the formed valve component 100. Thus, the fold line 303 can also be considered a bottom edge 304 of the leaflet section 301. Furthermore, in embodiments where no annular cuff 308 is desired, the cuff section 302 will be omitted and the bottom edge 304 will delimit the blank 300.

Thus, the leaflet section 301 comprises an arcuate top edge 305, the bottom edge 304 (which is also arcuate), a left side edge 306 and a right side edge 307. The left and right side edges 306, 307 are linear and extend between the arcuate top and bottom edges 305, 304. The arcuate top and bottom edges 305, 304 extend substantially parallel to one another while the left and right side edges 306, 307 extend at an angle β with respect to one another. In an embodiment of the blank 300 that has been found to optimize leaflet 112-114 performance in the formed valve component 100, the angle β is selected to be between 31° to 33°, and in a more specific embodiment the angle β is selected to be approximately 32°.

The left and right side edges 306, 307 of the leaflet section 301 have a length $L_L$. In the exemplified embodiment, the length $L_L$ is equal to the height $H_S$ (FIG. 10). In one embodiment, the length $L_L$ is in a range of 13 to 15 mm, and in a more specific embodiment the length $L_L$ is approximately 14 mm. The arcuate top edge 305 has a first radius of curvature while the arcuate bottom edge 304 has a second radius of curvature. In one embodiment, the first radius of curvature is in a range of 129 to 131 mm, and in a more specific embodiment the first radius of curvature is approximately 130 mm. The second radius of curvature is in a range of 115 to 117 mm, and in a more specific embodiment the second radius of curvature is approximately 116 mm.

In an embodiment of the blank 300 that optimizes performance of the formed valve component 100, the length $L_L$ and the second radius of curvature are selected so that the ratio of the second radius of curvature to the length $L_L$ is in a range of 8.1 to 8.5, and in a more specific embodiment a ratio of approximately 8.3.

The cuff section 302 extends from a bottom edge 308 to the fold line 303. When the valve component 100 is formed, the bottom edge 308 of cuff section 302 forms the top edge 131 of the annular cuff 108. In the exemplified embodiment, the bottom edge 308 is formed into the desired saw-tooth configuration of the top edge 131 of the annular cuff 108 discussed above. The cuff section has a length $L_C$. In one embodiment, the length $L_C$ is in a range of 13 to 15 mm, and in a more specific embodiment the length $L_C$ is approximately 14 mm. The left and right side edges 309, 310 of the cuff section are co-linear with the left and right side edges 306, 307 of the leaflet section 301. The left side edges 306, 309 of the leaflet section 301 and the cuff section 302 collectively form a left side edge 313 of the blank 300. Similarly, the right side edges 307, 310 of the leaflet section 301 and the cuff section 302 collectively form a right side edge 314 of the blank 300.

Immediately below the fold line 303, a suture boundary line 311 is illustrated. A suture free section 312 is formed between the fold line 303 and the suture boundary line 311. The suture free section 312 delineates the area of blank that is kept free of sutures or other fasteners so that any anchoring penetrations in the to-be-formed annular sleeve 304 are spaced from the inlet edge 309 by a desired axial distance, which is equal to distance a. In the exemplified embodiment, the distance a is approximately 1 mm.

Referring now to FIG. 6, once the blank 300 is formed as illustrated in FIG. 5, the annular belt 105, which is in the form of flat arcuate strip of sheet material, is properly positioned and affixed to the blank 300. More specifically, when the annular belt 105 is in flat strip form, the bottom edge 133 of the annular belt 105 is an arcuate edge having a radius of curvature that matches the first radius of curvature of the fold line 303 (which is also the bottom arcuate edge 304 of the leaflet section 301). The annular belt 105, when in flat strip form, also comprises an arcuate top edge 140 that is substantially parallel to the arcuate bottom edge 133.

The annular belt 105 can be formed by cutting a sheet of material, such as natural tissue or a pliable polymeric sheet, to the proper geometry and dimensions. In certain other embodiments, the annular belt 105 can be formed of a rigid or semi-rigid material, such as biocompatible polymers. In the exemplified embodiment, the annular belt 105 is a separate and distinct component than the frame 200. Once formed, the annular belt 105, in flat strip form, is overlaid atop the blank 300 so that the bottom edge 133 is substantially coextensive with the fold line 303. The annular belt 105, in flat strip form, is then affixed to the blank 300 along the arcuate top edge via fasteners 135, which are exemplified as sutures, to form the seam 136. As can be seen in FIG. 6, the geometry and dimensions of the annular belt 105, in flat strip form, is substantially identical to the cuff section 302 of the blank 300 with the exception of the saw-toothed edge portion.

Once the assembly of the blank 300 and the annular belt 105 (in flat strip form) of FIG. 6 is created, the blank 300 is rolled about so that the side edges 313, 314 of the blank 300 are slightly overlapped, as shown in FIG. 7. Referring now to FIG. 7, once the blank 300 is rolled as described above, the overlapping edges 313, 314 are affixed together, thereby forming the annular sleeve 104, which at this point in the formation process is in the form of an elongated truncated cone 150 having a single axial seam 127. The overlapping edges 313, 314 are affixed together via fasteners, which in the exemplified embodiment are sutures. In other embodiments, however, the affixing may be accomplished via staples, clamps, adhesives, fusing, or combinations thereof.

Once the annular sleeve 104 (in truncated cone 150 form) is formed, the annular sleeve 104 is aligned with the frame 200 as shown in FIG. 8. Referring to FIG. 8, it can be seen that the annular belt 105 is located within the annular sleeve 104 (in truncated cone 150 form) at this stage. The annular sleeve 104 (in truncated cone 150 form) is positioned so that the saw-toothed bottom edge 308 of the cuff section 302 (which will become the top edge 131 of the annular cuff 108) is closest to the tubular body 201 of the frame 200. The annular sleeve 104 (in truncated cone 150 form) is then translated axially upward so that the cuff section 302 enters the cavity 206 of the tubular body 201 of the frame 200. This translation of the annular sleeve 104 (in truncated cone 150 form) continues until the saw-toothed edge 308 of the cuff portion 302 becomes aligned with the struts 209 within the circumferential row E, as shown in FIG. 9.

Figure 9:
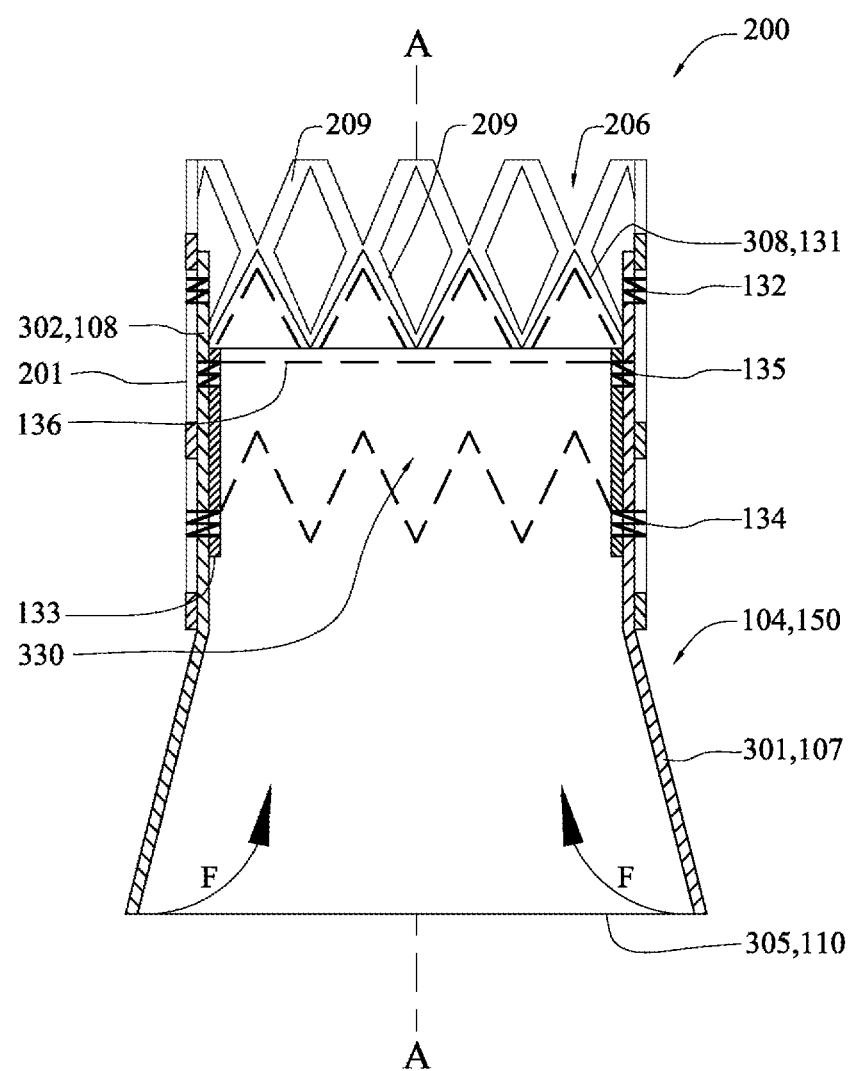
FIG. 9 is an axial cross-sectional schematic of the annular sleeve of FIG. 7 positioned within and anchored to the frame of the prosthetic valve device of FIG. 1, according to some embodiments of the present invention.

Referring now to FIG. 9, once the annular sleeve 104 (in truncated cone 150 form) is so positioned the cuff section 302 of the annular sleeve 104 (in truncated cone 150 form) is anchored to the tubular body 201 of the frame 200 by the fasteners 132. In the exemplified embodiment, the saw-toothed bottom edge 308 is anchored to the tubular body 201 of the frame 200 by fasteners 132 that run in a saw-toothed configuration about the circumference of the saw-toothed bottom edge 308, thereby anchoring the saw-toothed bottom edge 308 to the struts 209 in the circumferential row E (see FIGS. 1 and 8). Of course, other types of fasteners, such as the ones mentioned above, could be used and/or different types of suturing techniques, in other embodiments of the invention.

The cuff section 302 of the annular sleeve 104 (in truncated cone 150 form) is further anchored to the tubular body 201 at a lower position (relative to the fasteners 132) of the frame via fasteners 134. In the exemplified embodiment, this additional anchoring is achieved by fasteners 134 that run in a saw-toothed configuration about the circumference of the cuff section 302 of the annular sleeve 104 (in truncated cone 150 form), thereby anchoring the annular sleeve 104 (in truncated cone 150 form) to the struts 209 in the circumferential row H (see FIGS. 1 and 8). Of course, other types of fasteners, such as the ones mentioned above, could be used and/or different types of suturing techniques in other embodiments of the invention.

The annular sleeve 104 (in truncated cone 150 form) is then folded in upon itself by pushing the leaflet section 301 of the annular sleeve 104 (in truncated cone 150 form) through the passageway 330 formed by the cuff section 301 (and the annular belt 105). This motion is schematically exemplified by the arrows F in FIG. 9.

Prior to the aforementioned folding (or subsequent thereto if desired), the commissures 115 (FIG. 2) are formed into the edge 305, 110. The commissures 115 are formed in a spaced-apart arrangement about the circumference of the edge 305, 110 as discussed above. This is accomplished by cinching portions 116 of the annular sleeve 104, 150 between opposing legs 117A-B of the commissure strips 106 and affixing the commissure strips 106 to the cinched portions 116 in the desired spaced-apart circumferential arrangement discussed above.

Once the annular sleeve 104, 150 is folded in on itself and the commissures 115 are formed therein as described above, the commissures 115 are anchored to the axial posts 207 of the tubular body 201 of the frame 200 as described above, thereby forming the prosthetic valve device 1000. The final arrangement is shown in FIGS. 1 and 10.

Figure 12:
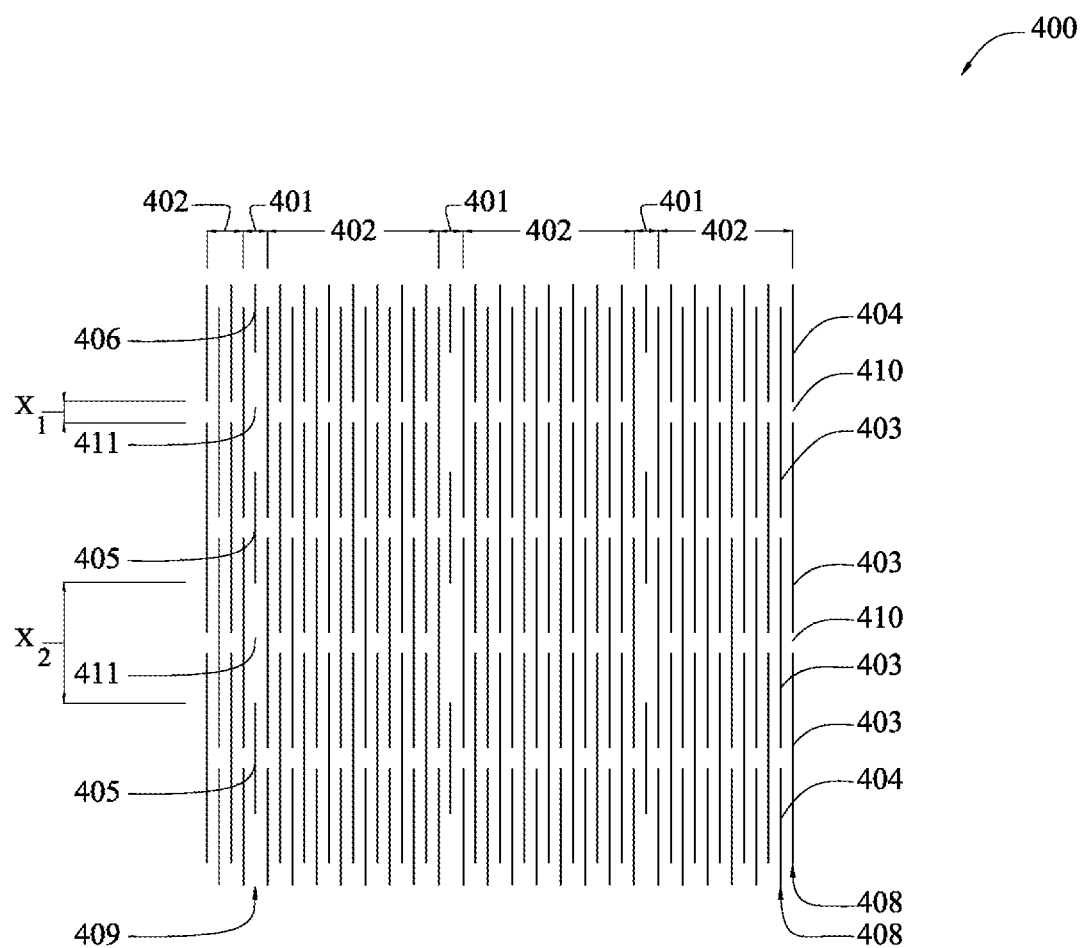
FIG. 12 is a 2-D rendering of a cutting pattern to be applied to a tube to form a frame for a prosthetic valve device, according to some embodiments of the present invention.
Figure 13:
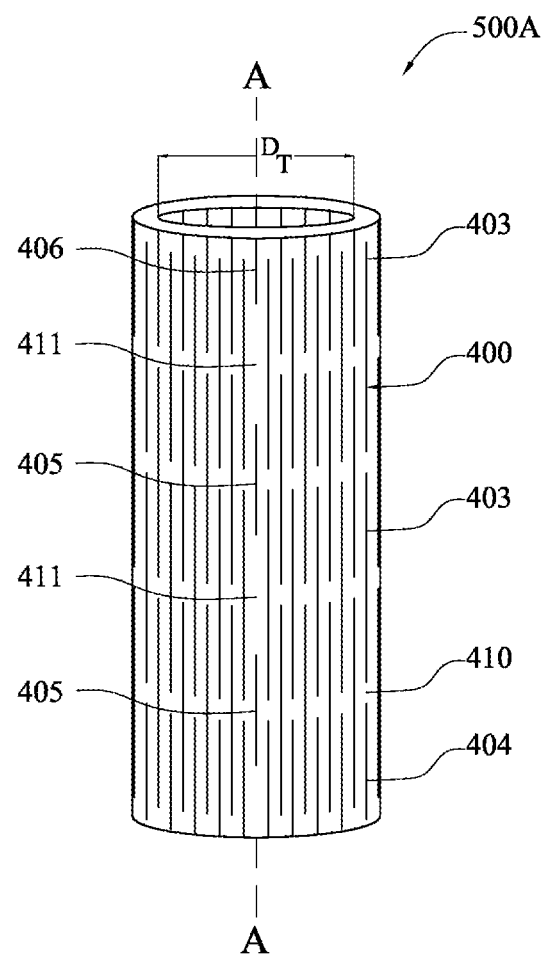
FIG. 13 is a perspective view of a tube with a pattern of slits cut into the tube in accordance with the cutting pattern of FIG. 12.
Figure 14:
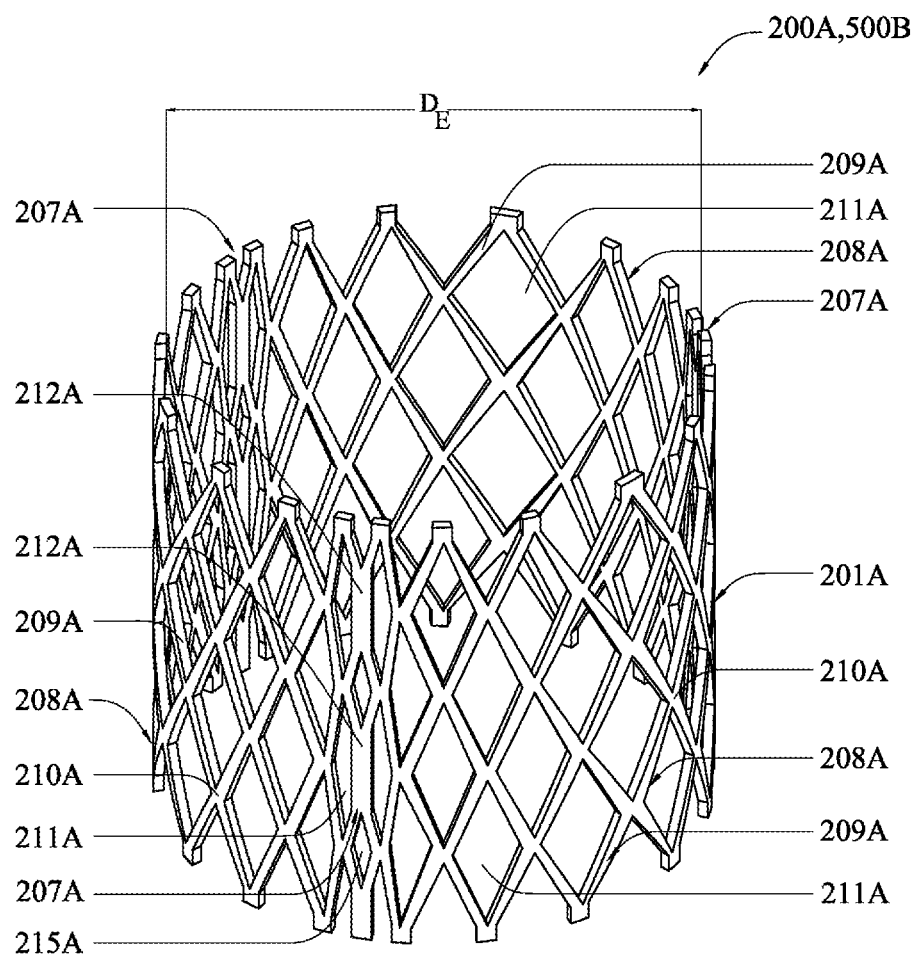
FIG. 14 is a perspective view of the tube of FIG. 13 wherein the tube has been diametrically expanded to form a frame according to some embodiments of the present invention.

Referring now to FIGS. 12-14, a method of forming a tubular body of a frame for a prosthetic valve device, and the resulting frame, will be described in accordance with an embodiment of the present invention.

A 2-D rendering of a cutting pattern 400 according to an embodiment of the present invention is illustrated in FIG. 12. The cutting pattern 400 is designed to be applied to 3-D tube 500A (FIG. 13) of memory shape material and then cut into the 3-D tube 500A as will be described in greater detail below. The 2-D pattern 400 is configured to include a plurality of post pattern sections 401 and a plurality of lattice pattern sections 402 that extend between the post pattern sections 401. In the exemplified embodiment, the cutting pattern 400 comprises three post pattern section 401 and thee lattice pattern sections 402 (the left-most and right-most sections of lattice pattern sections 402 being considered a single section 402). As will be described in greater detail below, the post pattern sections 401 are designed to form the axial posts 207A in the tubular frame 201A of the resulting frame 200A (FIG. 14) while the lattice pattern sections 401 are designed to form the lattice structures 208A in the tubular frame 201A of the resulting frame 200A.

As can be seen, the cutting pattern 400 is formed entirely of linear slits 403-406, which in the exemplified embodiment, all extend substantially parallel to one another and vertically. Thus, when the cutting pattern 400 is applied to the 3-D tube 500A, all of the slits 403-406 extend substantially parallel to the axis A-A of the tube 500 (shown in FIG. 13).

All of the linear slits 403-406 of the cutting pattern 400 are arranged in vertical columns (which become axial columns when applied to the 3-D tube 500A). In the exemplified embodiment, there are only four different lengths of slits used to create the entire cutting pattern 400. Each column 408 of slits in the lattice pattern sections 402 are formed by two longer slits 403 and one shorter slit 404. The columns 408 of the lattice pattern sections 402 are arranged in an offset alternating manner due to the fact that the positioning of the shorter slit 403 in adjacent columns 408 alternates between the top edge and the bottom edge. Each of the post pattern sections 401 are formed by a single column 409 of two longer slits 405 and a short slit 406.

Adjacent slits 403, 404 in the same columns 408 of the lattice pattern sections 402 are separated by gaps 410 having a first vertical distance $x_1$ (which can be considered a first axial distance when applied to the 3-D tube 500A). Similarly, adjacent slits 405, 406 in the same columns 409 of the post pattern sections 401 are separated by gaps 411 having a second vertical distance $x_2$ (which can be considered a second axial distance when applied to the 3-D tube 500A). Because the second axial distance $x_2$ is greater than the first axial distance $x_1$, a clear distinction between the post pattern sections 401 and the lattice pattern sections 402 is visible within the cutting pattern 400. In one embodiment, the second axial distance $x_2$ is 4 to 5 times greater than the first axial distance $x_1$.

As will become apparent from the discussion below, when the frame 200A is formed using the cutting pattern 400 as described below, the gaps 410 of the lattice pattern sections 402 form nodes 210A within the lattice structures 208A of the tubular body 201A of the frame 200A while the gaps 411 of the post pattern sections 401 form axially elongated nodes 212A within the axial posts 207A.

Referring now to FIG. 13, once the 2-D rendering of the cutting pattern 400 is generated, it is applied to a 3-D tube 500A of a shape memory material, such as nickel titanium. Of course other shape memory materials can be used. The 3-D tube 500A has a first inner diameter $D_T$. The cutting pattern 400 is applied to the 3-D tube 500A so as to circumferentially surround the 3-D tube in a uniform manner. The cutting pattern 400 is applied to the 3-D tube 500A, in one embodiment, by laser cutting the slits 403-405 through the thickness of the 3-D tube 500A in the illustrated pattern. Of course, other cutting or formation techniques can be utilized as desired.

Once the cutting pattern 400 has been applied to the 3-D tube 500A, the 3-D tube 500A is diametrically expanded until it has a second inner diameter $D_E$, thereby becoming an expanded 3-D tube 500B, which is the tubular body 201A of the frame 200A (FIG. 14). The second inner diameter $D_E$ is greater than the first inner diameter $D_T$. In one embodiment, the first and second inner diameters $D_T$, $D_E$ are selected so that a ratio of the second inner diameter $D_E$ to the first inner diameter $D_T$ is in a range of 4:1 to 6:1. Methods and techniques for diametrically expanding the 3-D tube 500A into the expanded 3-D tube 500B utilizing mandrels and heating techniques are known in the art and require no further discussion herein.

Referring now to FIGS. 12-14 concurrently, as a result of the diametric expansion of the 3-D tube 500A, the slits 403-406 of the applied cutting pattern 400 are circumferentially stretched to form open cells 211A in the lattice structures 208A and open cells 215A in the axial posts 207A. More specifically, the slits 405, 406 of the post pattern sections 401 are transformed into the open cells 415A while the slits 403, 404 of the lattice pattern sections 402 are transformed into the open cells 411A. Further, the gaps 410 of the lattice pattern sections 402 are transformed into the nodes 210A within the lattice structures 208A while the gaps 411 of the post pattern sections 401 are transformed into the axially elongated nodes 212A within the axial posts 207A.

The expanded tube 500B (which is the tubular body 201A of the frame 200A), comprises a plurality of the axial posts 207A arranged about the expanded tube 500B in a circumferentially spaced-apart manner and a plurality of the lattice structures 208A which comprise the open cells 211A therein extending between the axial posts 207A. Because the frame 200A is formed by a single tube, the lattice structures 208A and the axial posts 207A are integrally formed as a unitary structure free of seams. All of the open cells 211A of the lattice structures 208A are of a diamond-shape or a partial diamond-shape.

Further, it is to be understood that the frame 200A can be utilized to form the prosthetic valve device 1000 interchangeably with frame 200. Thus, the discussion of the frame 200 and its interaction with the valve component 100 is also applicable to the frame 200A.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The invention claimed is:

1. A method for treating, preventing or ameliorating a symptom associated with a disease, disorder, or condition caused by a dysfunctional mammalian valve, comprising:
    providing a prosthetic valve device comprising:
        a frame comprising a tubular body; and
        a valve component disposed within and anchored to the tubular body of the frame, the valve component comprising:
        an annular sleeve having an annular inner wall that forms a fluid passageway along an axis from an inlet edge to an outlet edge, the annular sleeve folded over at the inlet edge to form an annular cuff that is concentric to and surrounds the annular inner wall and extends from the inlet edge toward the outlet edge; and
        an annular belt positioned between the annular inner wall and the annular cuff and having a bottom edge adjacent to a bight portion of the annular sleeve that forms the inlet edge; and
    delivering said prosthetic valve device to an implantation site in a mammalian subject in need thereof.

2. The method according to claim 1, wherein the annular sleeve and the annular belt comprise a biological tissue.

3. The method according to claim 1, wherein the prosthetic valve device is configured for transluminal delivery.

4. The method according to claim 1, wherein the disease, disorder, or condition is caused by a dysfunctional valve selected from: an aortic valve, a mitral valve; and a pulmonary cardiac valve.

5. The method according to claim 4, wherein the dysfunctional valve is an aortic valve.

6. The method according to claim 1, wherein the disease, disorder, or condition is selected from: aortic stenosis; valve regurgitation; and calcification of the leaflets.

7. The method according to claim 1, wherein the leaflets are free of affixing penetrations.

8. The method according to claim 1, wherein the leaflets are free of anchoring penetrations.

9. The method according to claim 1, wherein the implantation site is a degenerated valve.

10. The method according to claim 1, wherein a compression fit between the prosthetic valve device and the body lumen is created at the implantation site.

11. The method according to claim 10, wherein the frame comprises a shape memory metal.

* * * * *